(12) United States Patent
Myers et al.

(10) Patent No.: US 7,691,896 B2
(45) Date of Patent: Apr. 6, 2010

(54) ANALOGS OF SALINOSPORAMIDE A

(75) Inventors: Andrew G. Myers, Boston, MA (US); Binyuan Sun, Boston, MA (US); Stona R Jackson, Seattle, WA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/028,024

(22) Filed: Feb. 8, 2008

(65) Prior Publication Data

US 2009/0054665 A1 Feb. 26, 2009

Related U.S. Application Data

(63) Continuation of application No. PCT/US2006/031314, filed on Aug. 10, 2006.

(60) Provisional application No. 60/707,021, filed on Aug. 10, 2005.

(51) Int. Cl.
*A61K 31/407* (2006.01)
*C07D 491/044* (2006.01)

(52) U.S. Cl. ................. 514/421; 548/453

(58) Field of Classification Search ............. 548/453
See application file for complete search history.

(56) References Cited

U.S. PATENT DOCUMENTS

| | | | |
|---|---|---|---|
| 5,340,736 A | 8/1994 | Goldberg | |
| 6,271,199 B2 | 8/2001 | Brand et al. | |
| 7,144,723 B2 | 12/2006 | Fenical et al. | |
| 2003/0157695 A1 | 8/2003 | Fenical et al. | |
| 2006/0287520 A1* | 12/2006 | Danishefsky et al. | 540/203 |

FOREIGN PATENT DOCUMENTS

| | | |
|---|---|---|
| WO | 2005/002572 A2 | 1/2005 |
| WO | 2007/021897 A1 | 2/2007 |

OTHER PUBLICATIONS

Reddy et al., An Efficient, Stereocontrolled Synthesis of a Potent Omuralide-Salinosporin Hybrid for Selective Proteasome Inhibition, 2005, J. Am. Chem. Soc., 127, pp. 8974-8976.*
Ciechanover, A., Cell, 1994, 79, pp. 13-21.
Cohen, J. Science, 1995, 267, pp. 960.
Collins, T., Lab. Invest., 1993, 68, pp. 499-508.
Corey et al., J. American Chemical Society, 2004, 126 (20), pp. 6230-6231.
Fenical et al., Angew. Chem. Int. Ed., 2003, 42, pp. 355-357.
Gonzalez et al., J. Exp. Med., 1996, 84, pp. 1909.
Kofron, et al. J. Org. Chem. 1976, 41, pp. 1879.
Kojima, S. et al., Fed. Eur. Biochem. Soc., 1992, 304, pp. 57-60.
Kumatori et al., Proc. Natl. Acad. Sci. USA, 1990, 87, pp. 7071-7075.
Palombella et al., Cell 1994, 78, pp. 773-785.
Pangborn, et al., Organometallics 1996, 15, pp. 1518.
Still, et al. J. Org. Chem. 1978, 43, pp. 2923.
Thanos et al., Cell 1995, 80, pp. 529-532.
Traenckner et al., MBO J. 1994, 13, pp. 5433-5441.
Tsubaki et al., Biochem. and Biophys. Res. Comm., 1993, 196, pp. 1195-1201.
Supplemental Search Report from EPO Appln. No. 06789692.8.
Office Action dated Nov. 17, 2009 from EPO Appln. No. 06789692.8

* cited by examiner

*Primary Examiner*—Kamal A Saeed
*Assistant Examiner*—Kristin Bianchi
(74) *Attorney, Agent, or Firm*—Banner & Witcoff Ltd.

(57) ABSTRACT

Disclosed herein are analogs of Salinosporamide A, having the Formula I as follows:

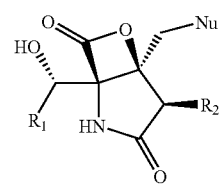

I

Like Salinosporamide A, the compounds of the present invention will inhibit the proteasome, an intracellular enzyme complex that destroys proteins the cell no longer needs. Without the proteasome, proteins would build up and clog cellular machinery. Fast-growing cancer cells make especially heavy use of the proteasome, so thwarting its action is a compelling drug strategy.

16 Claims, 8 Drawing Sheets

Fig. 1 - Scheme I

Fig. 2 - Scheme II

Fig. 3 - Scheme III

Fig. 4 - Scheme IV

Fig. 5
A. ¹H NMR scan of authentic 7,8-dihydrosalinosporamide (in d6-DMSO) Scanned from patent application WO 2005/003137):
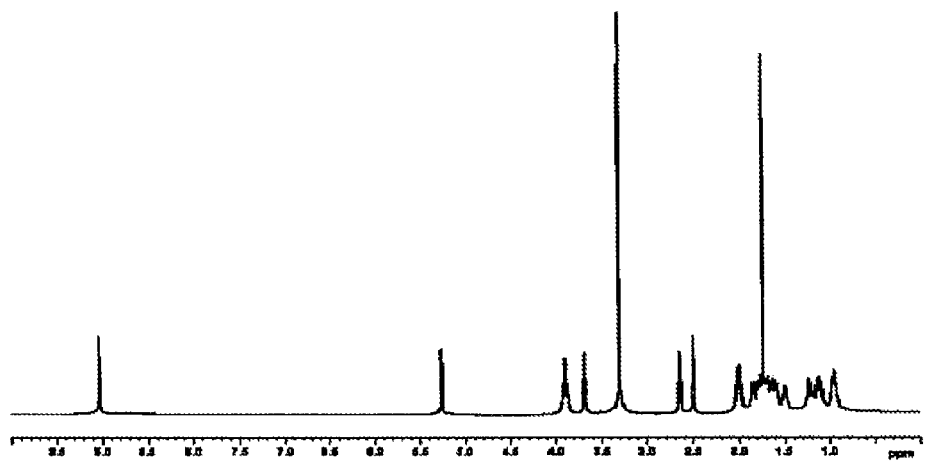
B. ¹H NMR scan of synthetic (±)-7,8-dihydrosalinosporamide (in d6-DMSO, 500 MHz)
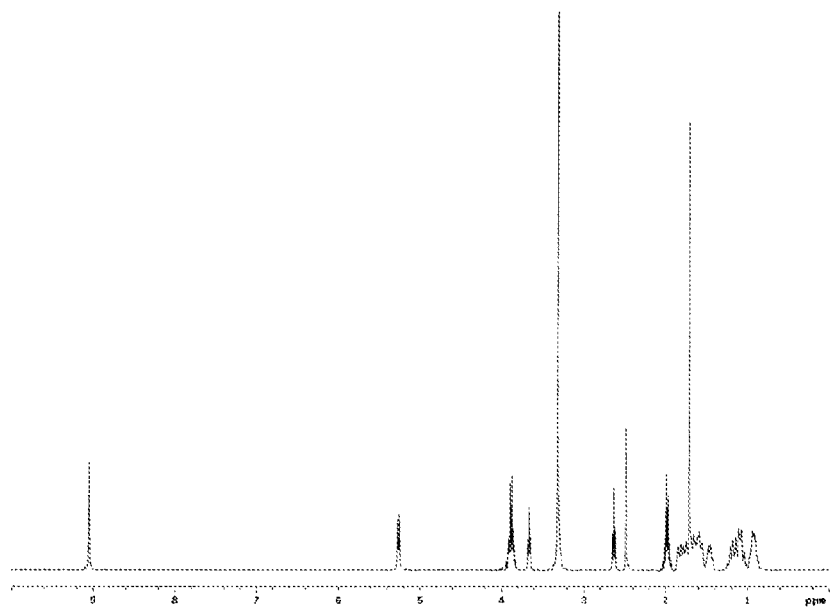

Fig. 6 - Determination of relative stereochemistry by X-Ray analysis

Fig. 7
Scheme V - Enantioselective Synthesis of Salinosporamide A Analogs
Part 1 - Using different chiral auxiliaries in the aldol reaction:
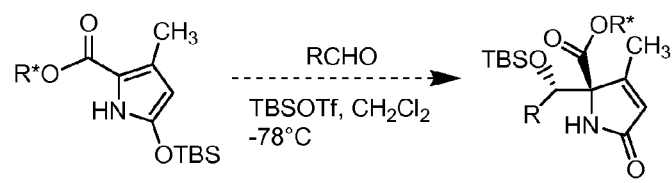
R*: Chiral Auxilliary
For example, R* can be:
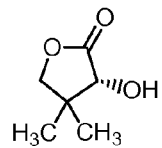
Pantolactone or its analogs
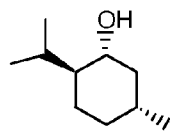
Menthol or other cyclohexyl based chiral auxiliaries
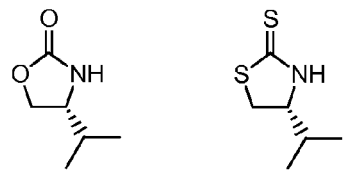
Oxazolidinone based chiral auxiliaries Part 2. Pantolactone as the chiral auxiliary:

ANALOGS OF SALINOSPORAMIDE A

CROSS-REFERENCE TO RELATED APPLICATIONS

This application is a continuation of PCT Application No. PCT/US2006/031314 filed 10 Aug. 2006 which was published in the English language on 22 Feb. 2007 as PCT Publication No. WO 2007/021897. The PCT Application claims priority from U.S. Provisional Application Ser. No. 60/707,021, filed 10 Aug. 2005. The disclosures of these applications are hereby incorporated herein by reference.

STATEMENT OF GOVERNMENT SUPPORT

This invention was made with government support under R37-CA04148 awarded by the National Institutes of Health. The government has certain rights in the invention.

BACKGROUND OF THE INVENTION

Salinosporamide A (1) was discovered by Fenical et al. as a bioactive product of a marine microorganism that is widely distributed in ocean sediments. See, Fenical et al., Angew. Chem. Int. Ed., 2003, 42, 355-357. More recently, a simple stereocontrolled total synthesis of salinosporamide A was reported by Corey et al., J. Amer. Chem. Soc., 2004, 126 (20) 6230-6231.

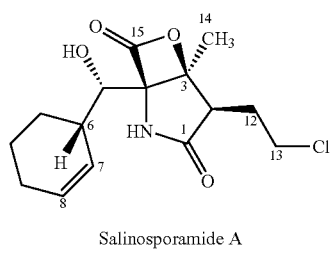

Salinosporamide A (1)

Salinosporamide A inhibits the proteasome, an intracellular enzyme complex that destroys proteins the cell no longer needs. Without the proteasome, proteins would build up and clog cellular machinery. Fast-growing cancer cells make especially heavy use of the proteasome, so thwarting its action is a compelling drug strategy. See, Fenical et al., U.S. Patent Publication No. 2003-0157695A1 and U.S. Pat. No. 7,144,723, the disclosures of which are hereby incorporated herein by reference.

SUMMARY OF THE INVENTION

One embodiment of the present invention comprises nucleophilic substituted analogs of Salinosporamide A, having the Formula I:

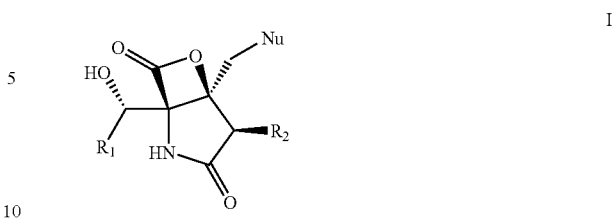

I wherein:

$R_1$ is selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, and halogen;

$R_2$ is selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, halogen and aryl; and Nu is a nucleophile.

In Formula I, $R_1$ is preferably selected from the group consisting of methyl, ethyl, propyl, iso-propyl, n-butyl, iso-butyl, and tert-butyl, each optionally substituted by halogen, preferably selected from Cl and F.

Alternatively, in Formula I, $R_1$ is preferably selected from the group consisting of cyclopropyl, cyclobutyl, cyclopentyl and cyclohexyl, each optionally with a double bond.

In Formula I, $R_2$ is preferably selected from the group consisting of methyl, ethyl, n-propyl, iso-propyl, n-butyl, iso-butyl and tert-butyl, each optionally substituted by one or more substituents selected from the group consisting of C1-C4 alkoxy, amido, halogen and aryl. Preferred halogens are Cl and F.

In Formula I, Nu is preferably selected from the group consisting of Iodide (I—), Hydrogen Sulfide (HS—), Carbsulfides (RS—); Bromide (Br—), Hydroxide (HO—), Carboxides (RO—), Cyanide (CN—), Azide (N3-); Amine (NH2-), Carb-amines (—NHR), Chloride (Cl—), Fluoride (F—), and Carboxylates (RCO2-). In the Carb-embodiments, the R groups are independently selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, halogen and aryl.

Another embodiment of the present invention provides synthetic methods for the formation of the compounds of Formula I and intermediate compounds associated therewith.

Another embodiment of the present invention is the compound (±) dihydro-salinosporamide A, having the Formula II:

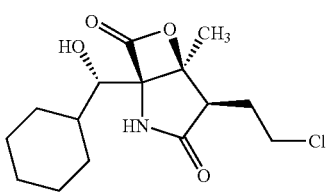

Another embodiment of the present invention provides a synthetic method for the formation of the compound of Formula II and intermediate compounds associated therewith.

Another embodiment of the present invention comprises the treatment of mammalian, preferably human, diseases with the compounds of the present invention. The compounds of the present invention are expected to possess the same range of activities exhibited by Salinosporamide A and the other related compounds, such as omuralide, lactacystin and the known analogs of lactacystin and clasto-lactacystin beta-lactone. See, Masse et al., Eur. J. Org. Chem., 2000, 2513-2528.

BRIEF DESCRIPTION OF THE DRAWINGS

FIG. 5, in parts A and B respectively, compares the $^1$H NMR scans of authentic 7,8-dihydrosalinosporamide with synthetic (±)7,8-dihydrosalinosporamide.

DETAILED DESCRIPTION OF THE INVENTION

As described above, one embodiment of the present invention provides nucleophilic substituted analogs of Salinosporamide A having the formula:

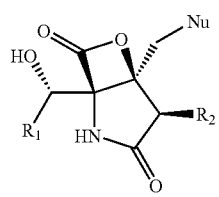

particularly wherein Nu is selected from the group consisting of Iodide (I—), Hydrogen Sulfide (HS—), Carb-sulfides (RS—); Bromide (Br—), Hydroxide (HO—), Carb-oxides (RO—), Cyanide (CN—), Azide (N$_3$—); Amine (NH$_2$—), Carb-amines (—NHR), Chloride (Cl—), Fluoride (F—), and Carboxylates (RCO—). In the Carb-embodiments, the R groups are independently selected from the group consisting of substituted or unsubstituted C1-C8 alkyl, substituted or unsubstituted C2-C8 alkenyl, substituted or unsubstituted C2-C8 alkynyl, substituted or unsubstituted, saturated or unsaturated, C3-C8 cycloalkyl, benzyl and substituted benzyl; wherein the substituent groups are independently selected from the group consisting of C1-C4 alkoxy, amido, halogen and aryl.

Figure 1:
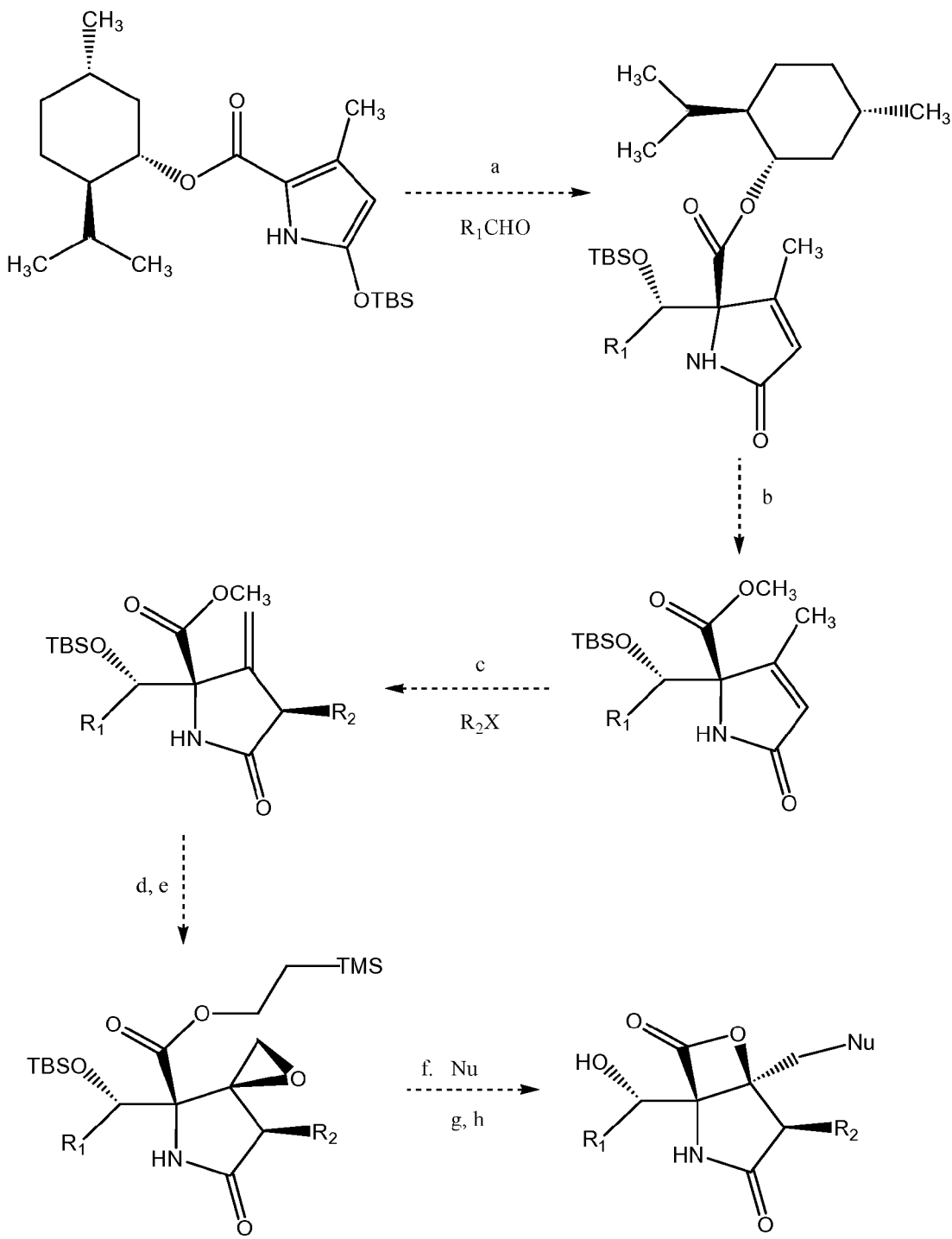
FIG. 1 is a synthetic scheme (Scheme I) for the preparation of the compounds of Formula I.

As shown in Scheme I (FIG. 1), the compounds of Formula I may be prepared by an enantioselective route that permits three points of structural diversity; R$_1$, R$_2$, and Nu, as defined herein.

The first step is the introduction of the R1 group to the intermediate compound (7)—the synthesis of which is described in Scheme III:

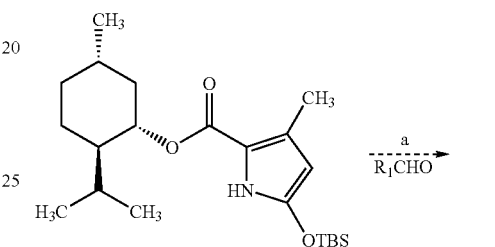

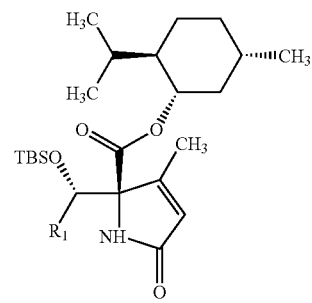

The preferred reactants are R$_1$CHO and TBSOTf in dichloromethane. The next step is the conversion of the R$_1$ containing compound to the following intermediate, by transesterification:

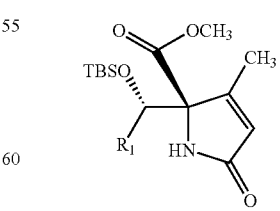

Reaction of the ester compound with R$_2$X with LDA and TMSCl in THF, affords the intermediate with the R$_2$ substituent in place:

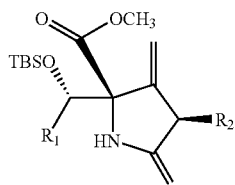

Reaction of this $R_1$ and $R_2$ containing intermediate—first with TMSCH$_2$CH$_2$OH, Ti(OiPr)$_4$; followed by CF$_3$CO$_2$H, Oxone, NaHCO$_3$, CH$_3$CN, H$_2$O, affords the epoxide intermediate with the following structure:

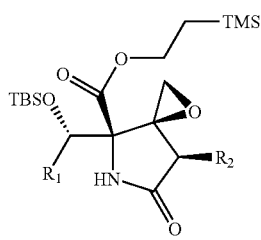

The epoxide intermediate affords the opportunity for nucleophilic substitution with preferred reagents being TfOH in dichloromethane, followed by BOPCl in pyridine and dichloromethane, to afford the compounds having Formula I:

Formula I

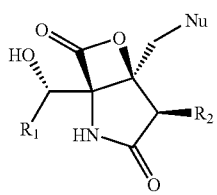

Alternatively, Nu in Formula I can R3, defined as for R1 and R2. In the dihydrosalinosporamide synthesis Nu was iodide. The iodide is quite likely to be a substrate for free-radical based transformations that could introduce an alkyl group. For example, reaction of the iodide with allyltributyltin in the presence of an initiator would quite likely give the product with R3=allyl. Similarly, reaction of the iodide with acrolein and tributyltin hydride would give R=CH$_2$CH$_2$CHO, acrylonitrile and tributyltin hydride would give CH$_2$CH$_2$CN, and the like. Also, it is expected that various organometallic reagents, such as organocopper reagents, will react either with the epoxide or with the iodide to introduce alkyl. The structure of the iodide that intercedes between structures 4 and 5 in the dihydrosalinosporamide route, is as follows:

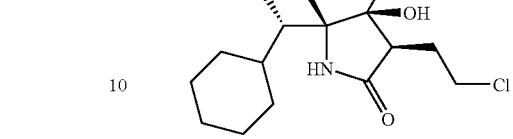

Figure 2:
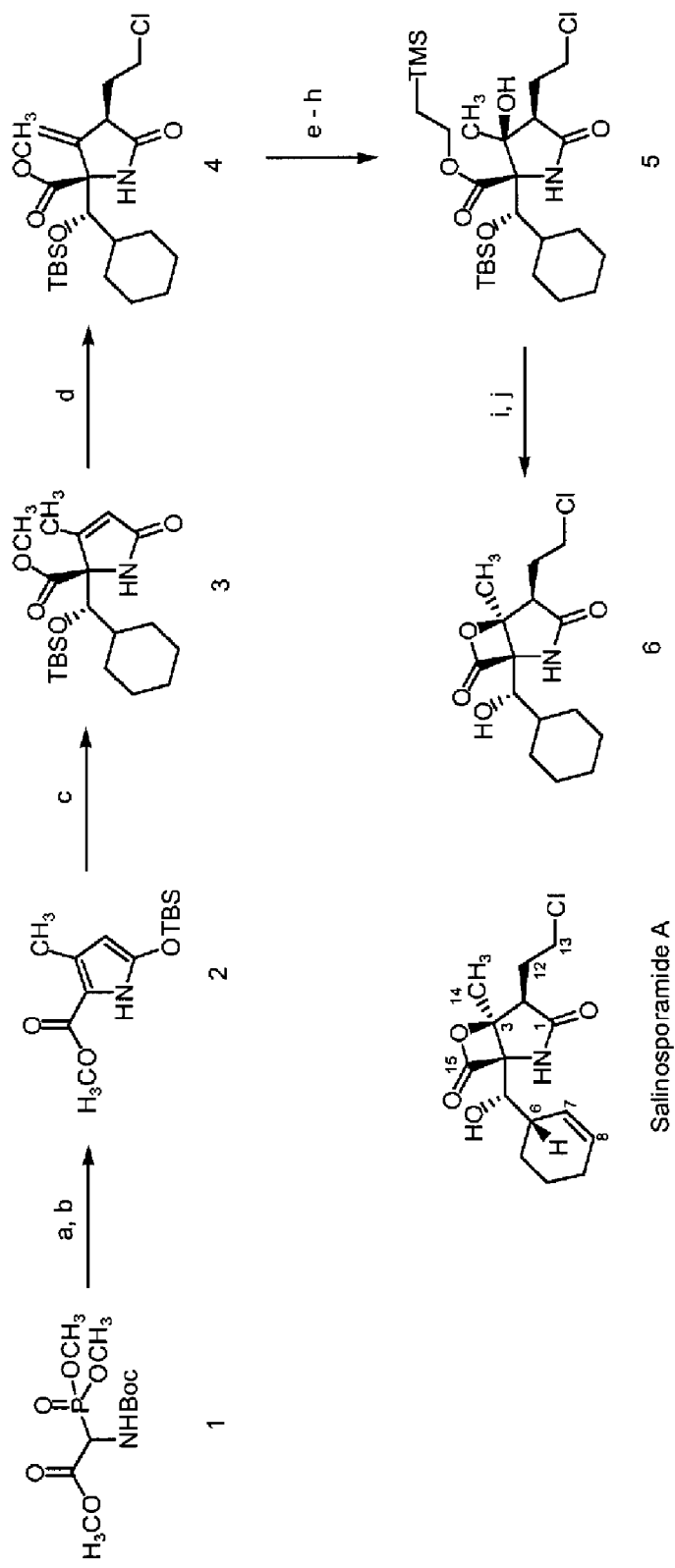
FIG. 2 is a synthetic scheme (Scheme II) for the preparation of the compounds of Formula II.

As shown in Scheme II (FIG. 2), the compound (±) dihydro-salinosporamide A, can be synthesized as follows.

Step 1:

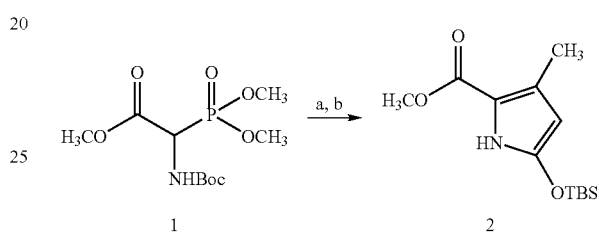

Compound 1 is first reacted with 2,2,6-trimethyl-4H-1,3-dioxin-4-one and 2,6-lutidine in refluxing toluene; followed by 2,6-lutidine and TBSOTf in dichloromethane at room temperature, to afford Compound 2.

Step 2:

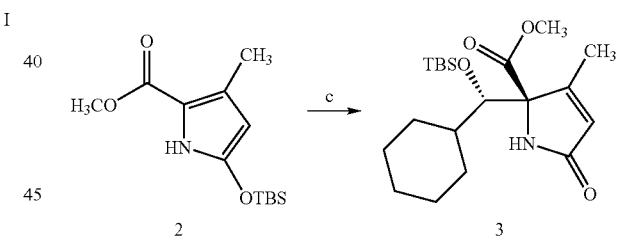

Compound 2 is reacted with cyclohexanecarboxaldehyde and TBSOTf in dichloromethane at −78° C., to afford Compound 3.

Step 3:

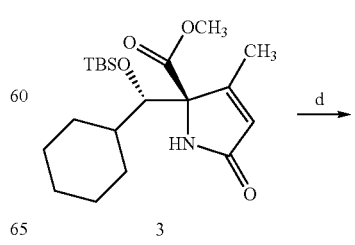

-continued

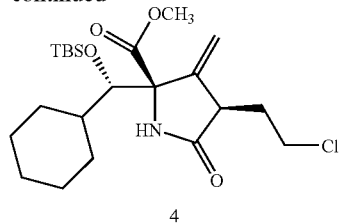

Compound 3 is converted to Compound 4 by reaction with TfOCH$_2$CH$_2$Cl, LDA, and TMSCl in THF at −78° C.

Step 4:

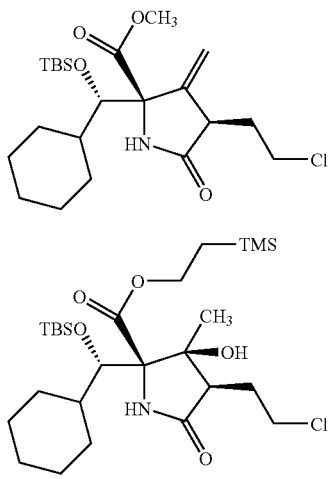

Compound 4 is converted to Compound 5 with the following series of reagents:
(e) TMSCH$_2$CH$_2$OH and Ti(OiPr)$_4$ at 100° C.;
(f) CF$_3$COCH$_3$ and Oxone/NaHCO$_3$ in CH$_3$CN/H$_2$O at 0° C.;
(g) MgI$_2$ in Et$_2$O at 23° C.; and
(h) H$_2$ over Raney Nickel at 23° C.

Step 5:

Compound 5 is converted to (±) dihydro-salinosporamide A (Formula II) in two steps, by treatment with:
(i) TfOH in CH$_2$Cl$_2$ at −30° C.; and
(j) BOPCl and pyridine in CH$_2$Cl at 23° C.

II

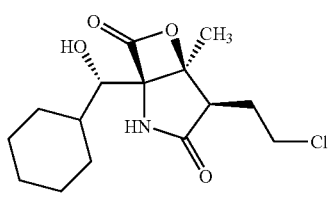

Figure 3:
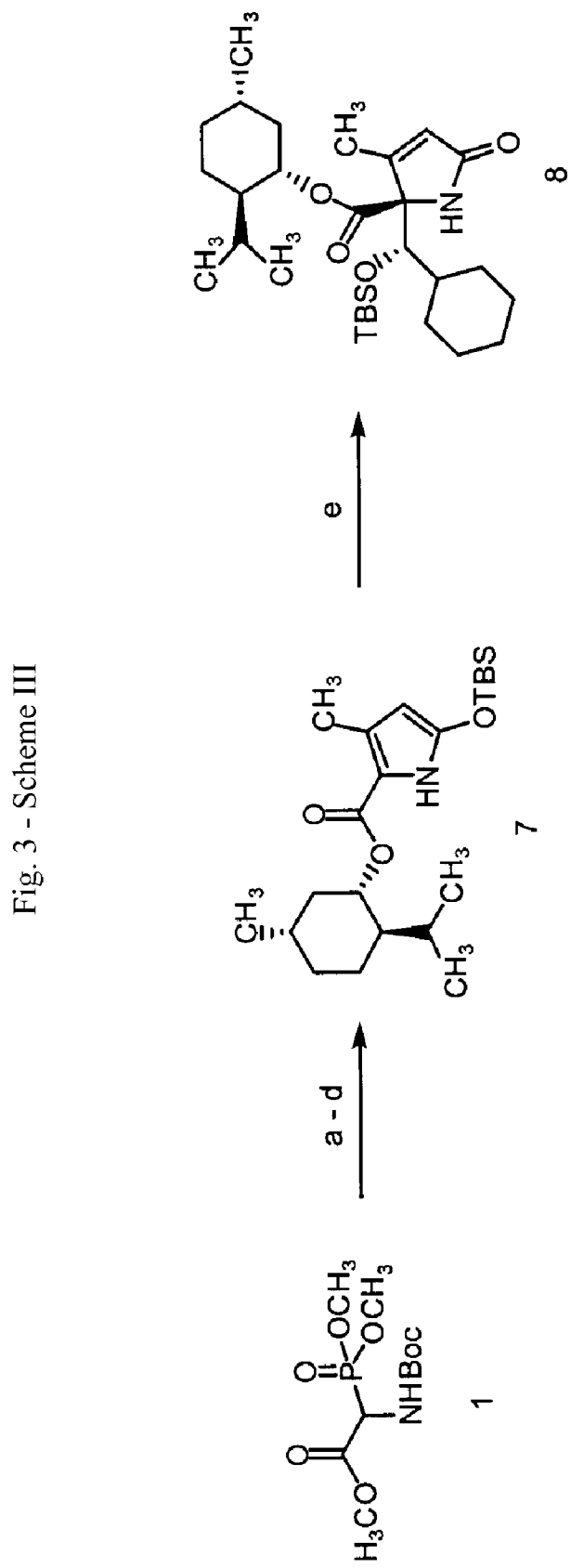
FIG. 3 is a synthetic scheme (Scheme III) for the preparation of intermediate compounds useful in the synthesis of the compounds of Formula I and Formula II.
Figure 4:
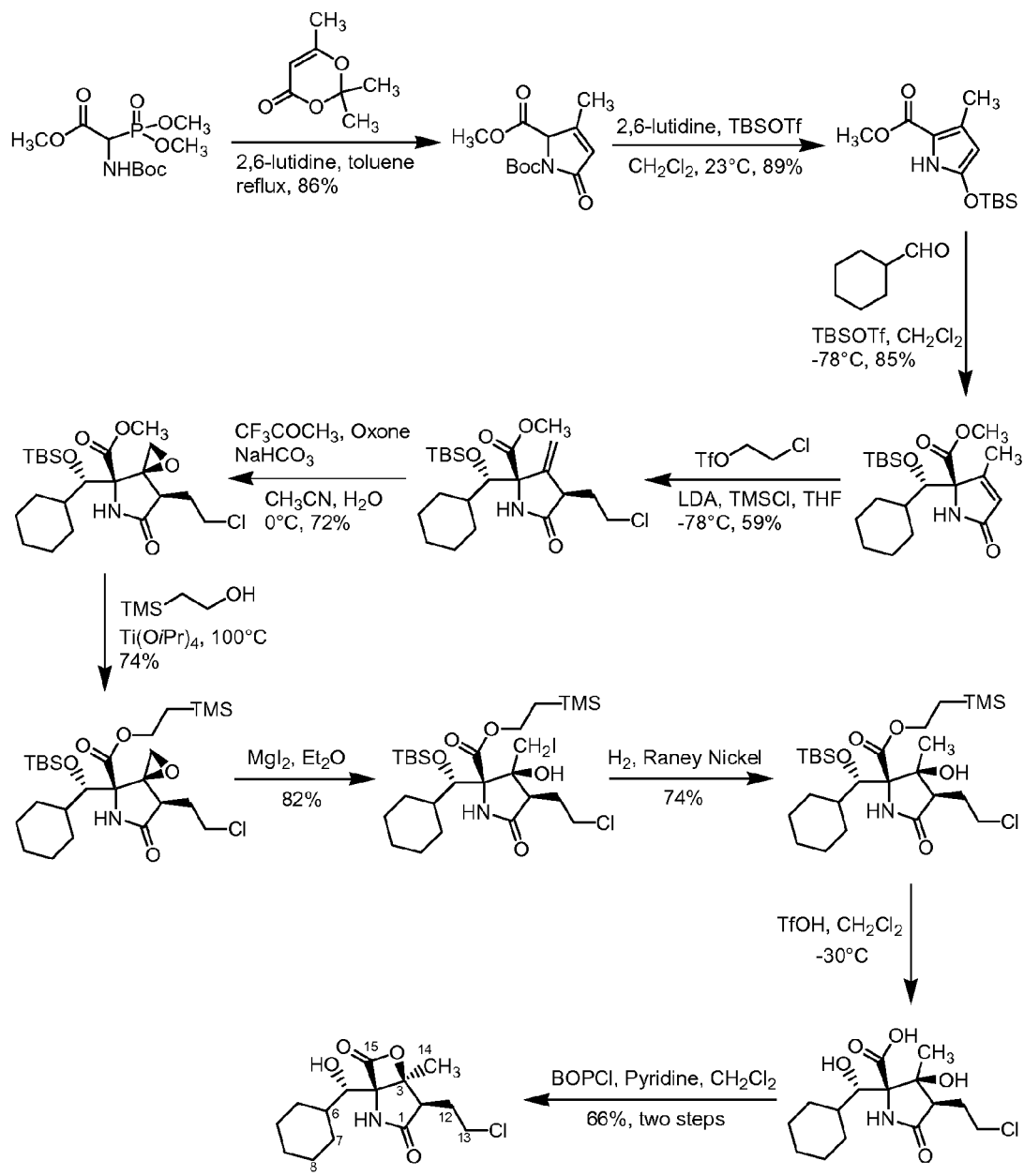
FIG. 4 illustrates Scheme IV, a racemic synthesis route for compounds of the present invention.
Figure 6:
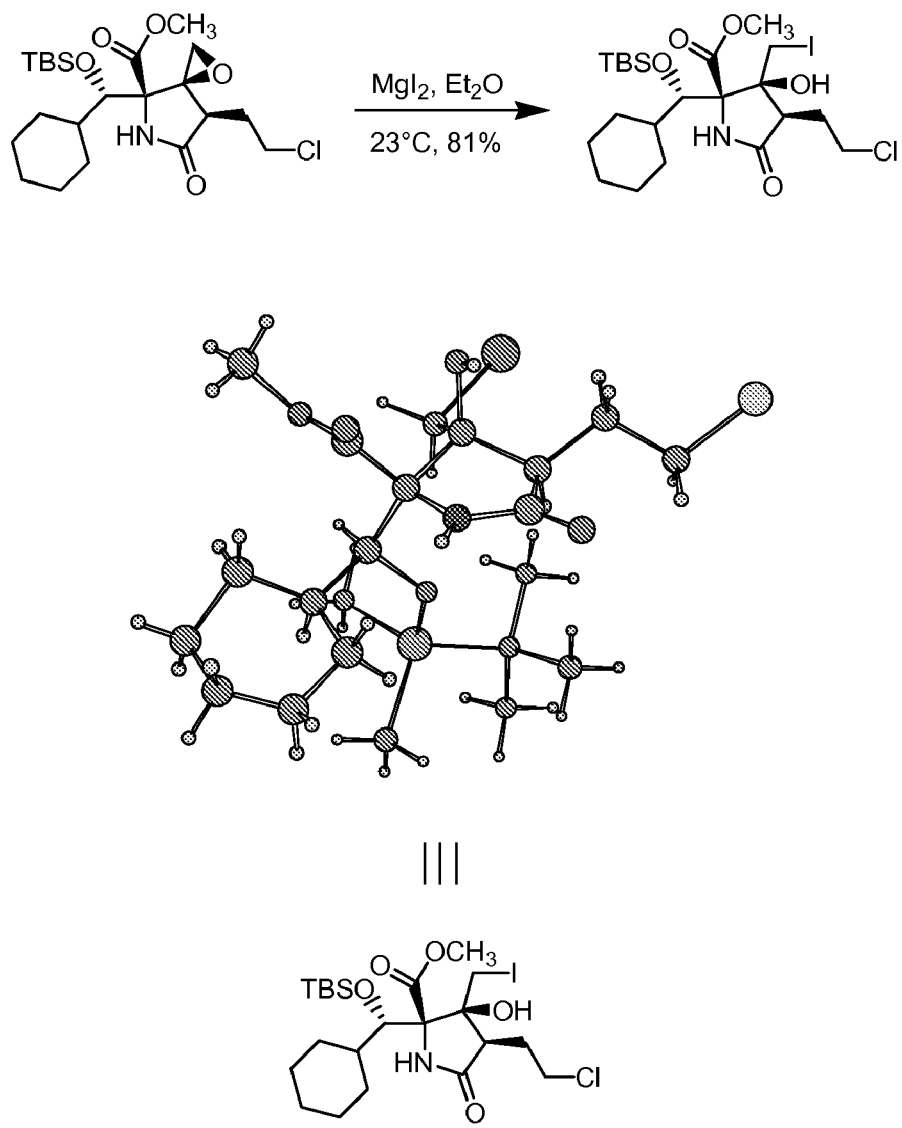
FIG. 6 provides details regarding the determination of the relative stereochemistry of the iodide intermediate made from Compound 8.
Figure 7:
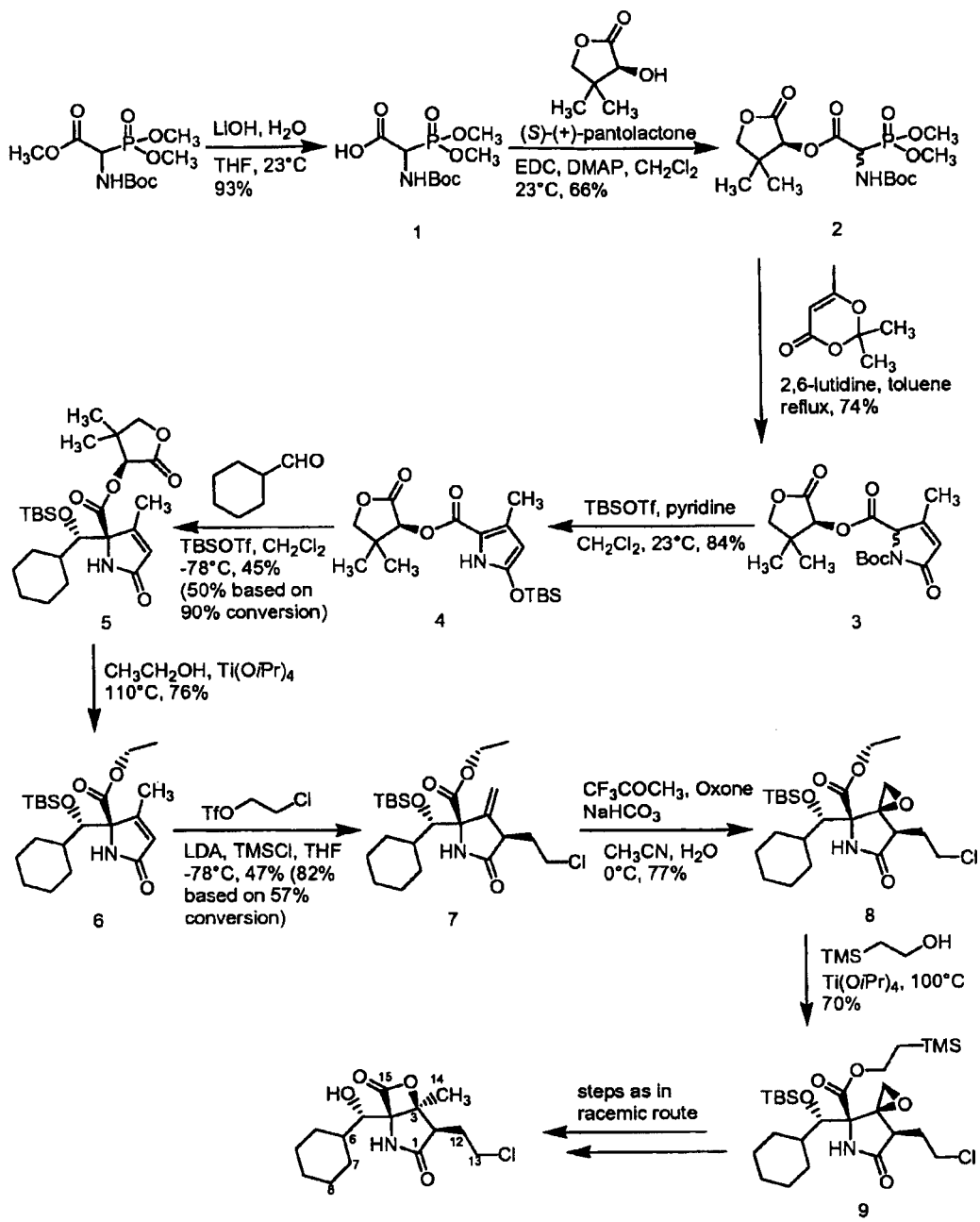
FIG. 7 provides details of Scheme V, in two parts (Part 1 and Part 2), the enantioselective synthesis of Salinosporamide A analogs of the present invention.

In Scheme III (FIG. 3) the synthesis of intermediate Compounds 7 and 8 is described from Compound 1:

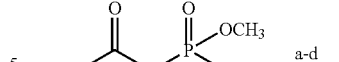

Step 1:

Compound 1 is converted to Compound 7 by the following series of reagents:
(a) LiOH in H$_2$O and THF at 23° C.;
(b) (−)-menthol, EDC and DMAP in CH$_2$Cl$_2$ at 23° C.;
(c) 2,2,6-trimethyl-4H-1,3-dioxin-4-one, 2,6-lutidine in refluxing toluene; and
(d) 2,6-lutidine and TBSOTf in CH$_2$Cl$_2$ at 23° C.

Step 2:

Compound 7 is converted into Compound 8 with cyclohexanecarboxaldehyde and TBSOTf in CH$_2$Cl$_2$ at −78° C.

Nucleophiles:

All molecules or ions with a free pair of electrons can act as nucleophiles. Examples of useful simple nucleophiles are: NH$_3$, OH$^−$, Cl$^−$, Br$^−$, and CN$^−$. Other examples of useful nucleophiles include, but are not limited to amines, hydrazines, alcohols, water, polyamines, polyols, amino alcohols, amino thiols, and dithiols.

Other useful nucleophiles are hydrogen sulfide, thioacetamide, acetamidine, ammonia, carbon monoxide, chloride, bromide, iodide or fluoride ions, bisulfide ion, hydroxyl ion, carbonate (CO$_3$); or acetate (CH$_3$CO).

For convenience, the following nucleophiles useful in this invention are grouped into mono-reactive nucleophiles, such as monoamine, hydrazine, and monohydric alcohol reagents, and poly-reactive nucleophiles such as polyamine, amino alcohol, and polyol reagents. Examples of each of these reagents follow.

Monoamine Reagents

Useful amines feature a NH$_2$ or NH group capable of reacting with the epoxide adducts of the present invention. The $NH_2$ or NH functional group can be attached to linear and/or branched alkanes having from about 1 to 100 carbons. Moreover, the $NH_2$, NH, or aminoalkyl groups can also be attached to homocyclic rings such as a cycloalkane having from 3 to about 18 members, aromatic rings, or fused aromatic rings as typified by benzene and naphthalene, respectively; heterocyclic rings, or fused heterocyclic rings having 5 or 6 members consisting of carbon, nitrogen, oxygen and sulfur as typified by pyrrole, furan, thiophene, imidazole, imidazoline, triazole, tetrazole, oxazole, thiazole, thiazoline, indole, benzofuran, benzothiophene, indazole, benzimidazole, benzotriazole, benzoxazole, purine, pyridine, pyridazine, pyrimidine, pyrazine, quinoline, isoquinoline, cinnoline, phthalazine, quinoxaline, phenathroline; hydrogenated versions of the above described heterocycles; and N-oxide, nitroxyl, proxyl, and tempo derivatives.

Other useful amine reactants can be selected from a wide assortment of heterocycles wherein the reactive NH functional group is actually a member of a heterocyclic ring having from about 3 to about 18 members selected from the group consisting of C, N, O, and S, as exemplified by morpholine and thiomorpholine.

Moreover, the presence of substituents in all of the above described amines is sometimes desirable, since the substituents of the present invention may impart useful multifunctional properties to the resulting products. Useful substituents include: ethers, polyethers,

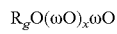

wherein $R_g$ is defined above, and ω is selected from the group consisting of ethylene, propylene, trimethylene, butylene, and tetramethylene, and x is an integer ranging from 1 to about 10; thioethers and polythioethers (replace O by S in the above formula); carboxy, carboxamide and nitrile groups; sulfur-oxygen substituents such as sulfoxide, sulfone, sulfonic acid, sulfonate ester, sulfonamide, and sulfate groups; phosphorus-oxygen substituents such as phosphoric acid, phosphonic acid, thiophosphoric acid, and thiophosphonic acid groups. The presence of these substituents in amine containing alkanes, homocycles, and heterocycles imparts new and useful properties to the additive products.

Examples of useful amines wherein the amino group is attached to linear and branched alkanes and cycloalkanes, and their substituted derivatives include: methyl, ethyl propyl, butyl, amyl, hexyl, heptyl, octyl, decyl, undecyl, dodecyl, tridecyl, tetradecyl, pentadecyl, hexadecyl, octadecyl, eicosyl, docosyl, and tricosylamine; isopropyl, isobutyl, sec-butyl, tert-butyl, 2-ethyl-propyl, S-(−)-2-methylbutyl, isoamyl, 1,2-dimethylpropYl, tert-amyl, 3,3-dimethylbutyl, 2-heptyl, 3-heptyl, 2-ethylhexyl, 1,5-dimethylhexyl, t-octyl, 2-decyl, 2-tetradecyl, 7-tetradecyl, 2-hexadecyl, 7-heptadecyl, 2-octadecyl, 9-octadecyl, 2-methyl-2-nona-decyl, 2-eicosyl, 9-heneicosyl, 2-docosyl, 2-octacosyl, 2-tri-cosyl, and 7-tricosylamine; dimethyl, diethyl, methylpropyl, methylisopropyl, dipropyl, diisopropyl, methylbutyl, dibutyl, di-sec-butyl, diisobutyl, dipentyl, dihexyl, dioctyl, bis-(2-ethyl-hexyl), didecyl, methyloctadecyl, dioctadecyl, didocosyl, diocta-cosyl, and ditricosylamine; cyclopropyl, cyclopentyl, cyclohexyl, dicyclohexyl, 4-methylcyclohexyl, cycloheptyl, cyclooctyl, cyclododecyl, (R)-(+)-bornyl, (−)-cis-myrtanyl, 1-adamantyl- and 2-adamantylamine. Useful substituted amines include: methoxy, ethoxy, 2-methoxyethyl, 3-methoxypropyl, 3-butoxypropyl, and 3-isopropoxypropylamine; glycine, iminodiacetic acid, sarcosine, alanine, leucine, beta-alanine, 4-aminobutyric acid, 8-amino-caprylic acid, 12-aminododecanoic acid, aspartic acid, glutamic acid, 3-aminoadipic acid, cysteine, penicillamine, homocysteine, S-methylcysteine, ethioneine, asparagine, glutamine, arginine, cyan-amide, 3,3'-iminodipropionitrile, taurine, 3-aminopropanesulfonic acid, 2-aminoethyl-phosphonic acid, 3-aminopropylphosphonic acid, and 6-amino-1-hexylphosphate and 1-amino-1-cyclohexanecarboxylic acid.

Examples of useful amines wherein an amino group or aminoalkyl group is attached to homocycles such as benzene and fused aromatic rings like naphthalene, and their substituted derivatives include: aniline, 4-methyl-4-butyl, 4-hexyl-, 4-octyl, 4-decyl, 4-dodecyl, 4-tetradecyl, 4-hexadecyl, 4-cyclohexyl aniline; p-methoxy, 4-butoxy, 4-hexyloxy and 4-methylmercaptoaniline; 5-aminoindan, 5-methoxy-2-methylaniline, 2,4-dimethoxyaniline, 2-aminobiphenyl, 4-phenoxyaniline, 4-(2-aminoethyl)benzenesulfonamide, 1-amino-naphthalene, 2-aminonaphthalene, benzylamine, aminodiphenylmethane, tritylamine, 2,2-diphenylamine, phen-ethylamine, 3-phenyl-propyl-amine, 3,3-diphenylpropylamine, 4-phenylbutylamine, 2-ethoxybenzylamine, 2-methoxy-phenethyl amine, 3,5-dimethoxybenzylamine, piperonylamine, 3,4-di-benzyloxyphenethylamine, 2,4,6-trimethoxy-benzylamine, 1-naphthyl methylamine, 1-aminofluorene and 9-amino-fluorene.

Examples of useful amines wherein an amino group or an aminoalkyl group is attached to a heterocycle, a substituted heterocyclic, or a fused heterocycle include: furfurylamine, 2-amino-2-thiophene-carboxylic acid, 3-thiophenemethylamine, 3-aminopyrazole, 2-aminoimidazole, 1-(3-aminopropyl)imidazole, hist-amine, histidine, 3-amino-1,2,4-triazole, 3-amino-5-mercapto-1,2,4-triazole, 5-amino-3-methylisoxazole, muscimol, ibotenic acid, 5-amino-3-methyl-isothiazole, 2-aminothiazole, 2-amino-5-phenyl-thiazole, 2-amino-4-phenyl-5-tetradecylthiazole, 2-amino-4-thiazole-acetic acid, 2-amino-1,3,4-thiadiazole, 5-amino-1,3,4-thiadiazole-2-thiol, 5-amino-3-phenyl-1,2,4-thiadiazole, indoline, tryptamine, alpha-methyltryptamine, 6-methoxytryptamine, tryptophan, tetrahydro iso quinoline, phenoxazine, phenothiazine, 2-aminobenzimidazole, 2-[aminomethyl]benzimidazole, 2-amino-benzoxazole, 2-aminobenzothia-zole, adenine, 2-aminopurine, 8-azaadenine, 2-aminopyridine, 2-aminoethylpyridine, 2-aminopyrimidine, 4-aminopyrimidine, 4-amino-2-mercaptopyrimidine, cytosine, 5-aminouracil, aminopyrazine, 3-amino-1,2, 4-triazine, 5-azacytosine, 3-aminoquinoline, 1-aminoisoquinoline, 4-amino-tempo, and 3-aminomethyl-1-proxyl.

Examples of useful amines wherein the amino group is a member of a heterocyclic ring include: aziridine, 2-methylaziridine, azetidine, pyrrole, pyrrolidine, pyrazole, imidazole, 2-ethyl-imidazole, 1H-1,2,3-triazole, 1,2,4-triazole, 1H-tetrazole, thi-azolidine, piperidine, 4-methyl piperidine, 4-phenylpiperidine, 4-benzylpiperidine, morpholine, 2,6-dimethylmorpholine, thio-morpholine, hexamethyleneimine, heptamethyleneimine, 1-aza-12-crown-4,1-aza-15-crown-5, and 1-aza-18-crown-6; substituted heterocycles include pyrrole-2-carboxylic acid, ethyl 4-pyrazole-carboxylate, 2-mercaptoimidazole, 4-phenylimidazole, tolazoline, urocanic acid, 4,5-dicyanoimidazole, and 1,2,3-triazole-4,5-di-carboxylic acid.

Hydrazines

Hydrazines useful in the present invention include hydrazine groups attached to alkanes, homocyclics, and heterocyclics as described above. Accordingly, the conversion of many of the above amine derivatives via suitable N-aminating agent, as in the preparation of N-aminoazoles as described in "Advances in Heterocylic Chemistry" Volume 53, pages 85-231 (1992), affords useful hydrazines. Examples of useful hydrazines include hydrazine, 1,1-dimethylhydrazine, 2-hydroxyethylhydrazine, 1-amino-pyrrolidine, N-aminopyrazole, N-aminoindazole, N-aminoimidazole, N-aminobenzimidazole, N-amino-1,2,3-triazole, N-aminobenzotriazole, N-aminotetrazole, N-aminothiazole, thiadiazole, and oxazole; 1-aminopiperidine, 1-aminohomopiperidine, 4-aminomorpholine, semi-carbazide, carbohydrazide, thiosemicarbazide, 4-ethyl-3-thiosemicarbazide, thiocarbohydrazide, aminoguanidine, 2-hydrazine-2-imid-azoline, phenylhydrazine, 1,1-diphenylhydrazine, 4-methoxy-phenyl-hydrazine, 4-phenyl-semicarbazide, 4-phenylthiosemicarbazide, benzenesulfonylhydrazide, 2-furoic hydrazide, 2-thiophenecarboxylic hydrazide, 4-amino-1,2,4-triazole, purpald, 2-hydrazino-pyridine, isonicotic hydrazide, 4-hydrazinoquinoline, hydralazine, dansyl hydrazine, 9-aminotheophylline, and N-aminopurines.

Monohydric Alcohols

Monohydric alcohols useful in the present invention include hydroxy alkanes, hydroxy and hydroxyalkyl containing homocycles, and heterocycles as well as their substituted derivatives by analogy with the amines described above.

Examples of useful alkanols and substituted alkanols include butyl, hexyl, octyl, decyl, dodecyl, tetradecyl, hexadecyl, octadecyl, eicosyl, docosyl, hexacosyl and triacontanyl alcohol; 2-methyl-1-pentyl, 2-propyl-1-pentyl, 3,7-dimethyl-1-octyl alcohol; 2-hexyl, 2-octyl, 4-decyl, 2-dodecyl, 2-hexadecyl alcohol; useful alicyclic alcohols include cyclopropylmethyl, cyclopentyl, cyclohexyl, cyclohexylmethyl, dicyclohexylmethyl, cycloheptyl, cycloheptylmethyl, cyclooctyl, cyclododecyl, cyclo-dodecylmethyl, 2-norbornanemethyl, fenchyl, myrtanyl, decahydro-2-naphthyl, 1-adamantyl and 1-adamantylmethyl alcohol; useful substituted alcohols include 2-ethoxyethanol, 2-butoxyethanol, 2-(2-ethoxy-ethoxy)ethanol, diethylene glycol dodecyl ether, dipropylene glycol methyl ether, triethylene glycol monomethyl ether, Brij 30, 35, 58, 78, Triton X-100, and 114; glycidol, 3-hydroxy-tetrahydrofuran, glycerol formal; 2-mercaptoethanol, 2,3-dimercapto-1-propanol, 2-methylthioethanol, 1,5-dithia-cyclooctan-3-ol; glycolic acid, 12-hydroxydodecanoic acid, methyl glycolate, ethyl 6-hydroxy-hexanoate, alpha-hydroxy-gamma-butyrolactone, 2-methylsulfonylethanol, and isethionic acid; useful aromatic-substituted alcohols include: phenol, 3-pentadecylphenol, 4-cyclopentylphenol, 4-butoxyphenol, 3,3-dimethoxyphenol, 1-naphthol, 4-benzyloxy-phenol, benzyl alcohol, 1-phenyl-1-decanol, benzhydrol, 4-butylbenzyl alcohol, 4-butoxy-benzyl alcohol, 3,4,5-trimethyoxybenzyl alcohol, 4-chromanol, 2-biphenylmethanol, 2-naphthalene-ethanol, 9-fluorenemethanol, di-benzosuberol, phenethyl alcohol, 4-phenyl-1-butanol, 6-phenyl-1-hexanol, and 3,4-dimethoxyphenethyl alcohol; 2-phenylthioethanol, thio-chroman-4-ol, 4-hydroxyacetophenone, 4-hydroxy-benzophenone, 4-hydroxybenzoic acid, salicylic acid, 1-hydroxy-2-naphthoic acid, methyl 4-hydroxyphenyl acetate, methyl salicylate, and methyl 4-hydroxymethyl benzoate; useful heterocyclic-substituted alcohols include furfuryl alcohol, 3-thiophenemethanol, 4-hydroxytempo, and 3-pyridylcarbinol N-oxide.

Polyreactive Nucleophiles

Polyamines

Useful polyamines and substituted polyamines feature two or more amino groups selected from NH$_2$ and/or NH—R(R as defined above) which are capable of reacting with the epoxides of the present invention. By analogy with monoamines, the amine groups can be attached to alkanes, homocycles, and heterocycles; in addition, the polyamine derivatives may also contain one or more substituents Useful polyamines feature two or more amino radicals such as NH$_2$ and/or NH, and are attached to alkanes or branched alkanes containing from about 2 to about ten thousand carbons. Other useful polyamines are those where the amino or aminoalkyl groups are attached to a homocycle, a heterocycle; or, wherein the NH groups of the polyamine are members of a heterocyclic ring having from about 6 to about 30 members. The cyclic polyamines may contain other heteroatoms such as oxygen and sulfur.

The presence of selected substituents in the polyamine can impart useful multifunctional properties to the end products. Accordingly, substituents selected from: carboxylic acid, carboxamide and nitrile groups, as well as sulfur-oxygen groups, and phosphorus-oxygen groups are useful. Also useful are ethers, polyethers, thioethers, and polythioethers.

Examples of polyamines bearing alkane and substituted alkane groups include: ethylenediamine (EDA), 1,3-propanediamine(PDA), 1,2-propanediamine, 1,4-butanediamine, 2-methyl-1,2-propane-diamine, 1,3-pentanediamine, 1,5-pentane-diamine, 2,2-dimethyl-1,3-propanediamine, 1,6-hexane-di-amine, 2-methyl-1,5-pentane-di-amine, 1,7-heptanediamine, N-methyl-EDA, N-ethyl-EDA, N,N-dimethyl-EDA, N,N-diethyl-EDA, N,N-dibutyl-EDA, N-methyl-PDA, N-propyl-PDA, N,N-dimethyl-PDA, N,N-diethyl-PDA, N,N-dibutyl-PDA, diethylenetriamine (DETA), N-2-aminoethyl-1,3-propane-di-amine, 3,3'-diamino-N-methyl-dipropylamine, 3,3'-imino-bis-propylamine, spermidine, bis-hexamethylentriamine, tri-ethylenetetramine(TETA), N,N'-bis-(3-aminopropyl)EDA, N,N'-bis(3-aminopropyl)-1,3-PDA, spermine, tris-2-amino-ethylamine, tetraethylenepentamine (TEPA), and pentaethylenehexamine (PEHA).

Useful examples of substituted polyamines include: ornithine, lysine, lanthionine, cystine, penicillamine disulfide, and diamino-pimelic acid.

Useful examples of polyamines containing homocyclic and heterocyclic groups, and substituted groups include: 4,4'-methylene-bis(cyclohexylamine), 1,2-diaminocyclohexane, 1,4-di-aminocyclohexane, 1,3-cyclohexane-bis-(methylamine), 1,4-cyclo-hexane-bis-(methylamine), N-cyclohexyl-PDA, and 1,3-adamantane-diamines; substituted aromatic polyamines: benzidine, 1,2-dianilinoethane, 2-aminophenyl disulfide, 4,4'-ethylenedianiline, 3,3'-methylenedianiline, 4,4'-methylenedianiline, o-tolidine, 4-aminophenyl disulfide, 3,3',5,5'-tetramethylbenzidine, 1,2-phenylenediamine, 3,3'-diaminobenzidine, 4-methoxy-1,2-phenyl-enediamine, 1,2,4,5-benzenetetramine, 1,3-phenylene diamine, 4-methoxy-1,3-phenylenediamine, 1,4-phenylenediamine, 4,4'diamino-di-phenylamine, N,N-diethyl-1,4-phenylenediamine, pararosaniline base, 3,3'dimethoxybenzidine, 3,3'dimethylnaphthidine, 2,3-di-aminonaphthaline, 1,1'-binaphthyl-2,2'-diamine, 2,7-di-amino-fluorene, 9,10-diaminophenanthrene, N-phenyl-EDA, 1,2-diphenyl-EDA, N,N'-dibenzyl-EDA, 1-phenylpiperazine, 4-aminophenyl sulfone, and 2,5-diaminobenzenesulfonic acid; useful substituted heterocyclics include: 1-(3-aminopropyl)imidazole, histamine, histidine, carnosine, 3,5-diamino-1,2,4-triazole, 2,4-diamino-5-phenyl-thia-zole, trypt-amine, 5-aminoindole, tryptophan, 5-amino-indazole, 6-aminopurine, adenine, guanine, 2-aminomethylpyridine, 2-(2-aminoethyl)pyridine, 2,6-diaminopyridine, 2,3-diamino-pyridine, 2,4-diaminopyrimidine, 2,4,6-triamino-pyrimidine, 2,4-diamino-6-mercaptopyrimidine, 4,5-diamino-2,6-dimercapto-pyrimidine, mel-amine, 4-aminoquinaldine, 8-amino-quinoline, 5-aminoisoquinoline, and thionin.

Useful examples of heterocycles wherein one or more of the NH groups of the polyamine are ring members include: 1-(2-aminoethyl)piperidine, 3-amino-piperidine, 4-aminomethyl-piperidine, 4-amino-2,2,6,6-tetramethyl piperidine, piperazide, 1-methylpiperazine, 1,4-diaminopiperazine, 1-(2-aminoethyl)-piperazine, 1,4-bis-(3-aminopropyl)-piperazine, tetra-hydro-pyrimidine, homopiperazine, 1,4,7-triazacyclononane, 1,5,9-triazacyclo-dodecane, cyclen, 1,4,8,11-tetra-aza-cyclotetradecane, 1,4,-8,12-tetraazacyclopentadecane, hexacyclen, 4-(2-aminoethyl) morpholine, 4-(3-aminopropyl) morpholine, and 1,4,10-trioxa-7,13-di-aza-cyclo-pentadecane.

Useful examples of substituted polyamines containing polyether groups capable of complexing with alkali and alkaline earth metals, include: polyoxyethylene diamines, polyoxypropylene diamines, and polyoxypropylene triamines.

Amino Alcohols

Amino alcohols are also effective nucleophiles. Useful amino alcohols and substituted amino alcohols feature one or more amino groups selected from NH2 and/or NH—R radicals (where R is as defined above), and one or more OH groups capable of reacting with one or more adducts of the present invention. Amino alcohol reagents used in designing effective dispersants feature amino radicals such as NH2 and/or NH, and one or more OH radicals attached to alkanes or branched alkanes containing from about 2 to about a hundred carbons.

The amino and aminoalkyl groups present in amino alcohol reactants can be attached to alkanes, homocycles, and heterocycles; moreover, each class of amino alcohol may contain one or more substituents.

Examples of aliphatic amino alcohols, and substituted derivatives include: ethanolamine, 3-amino-1-propanol, 2-amino-1-pro-panol, 4-amino-1-butanol, 2-amino-1-butanol, 2-amino-2-methyl-1-propanol, 5-amino-1-pentanol, 2-amino-1-pentanol, 2-amino-3-meth-yl-1-butanol, 6-amino-1-hexanol, 2-amino-1-hexanol, isoleucinol, leucinol, serinol, 1-amino-1-cyclopentanemethanol, 2-aminocyclo-hexanol, 4-amino-cyclo-hexanol, 1-aminomethyl-cyclohexanol, 3-aminomethyl-3,5,5-trimethyl-cyclohexanol, 2-[2-amino-ethoxy]-ethanol, 2-methyl-aminoethanol, 2-ethylaminoethanol, 2-propyl-aminoethanol, diethanolamine, N,N-diethylethanol-amine, 3-di-methylamino-1-propanol, 3-amino-1,2-propanediol, N-ethyl-di-ethanolamine, triethanolamine, 3-dipropylamino-1,2-propanediol, 2-amino-2-ethyl-1,3-propanediol, bis-homotris, tris-(hydroxy-methyl)amino-methane (THAM), 2,2-bis-(hydroxymethyl)-2,2',2"-nitrilo-triethanol, 1,3-diamino-2-hydroxypropane, 2-(2-amino-ethylamino) ethanol, 1,3-bis-(dimethylamino)-2-propanol, N,N'-bis-(2-hydroxyethyl)-ethylenediamine, 1,3-bis-tris(hydroxymethyl) methylaminopropane, pentrol, 1-amino-1-deoxy-D-sorbitol, N-methyl-D-glucamine, disorbityl-amine, D-galactosamine, D-glucosamine, 1-(2-hydroxyethyl)pyrrolidine, 3-pyrrolidino-1,2-propanediol, 3-pyrrolidino-1,2-pyrrolidine-methanol, 1-methyl-2-pyrrolidine-ethanol, 1-piperidineethanol, 3-piperidino-1,2-propanediol, 2-piperidinemethanol, 2-piperidineethanol, 3-hydroxy-piperidine, 1-ethyl-4-hydroxypiperidine, 3-morpholino-1,2-propane-diol, tricine, bicine, serine, isoserine, homo-serine, threonine, 3-hydroxy-norvaline, muramic acid, 5-hydroxy-lysine, and 4-hydroxy-proline.

Examples of amino alcohols and alkane amino alcohols con-taining homocyclic and heterocyclic groups include: 2-amino-phenol, 2-amminobenzylamine, 2-aminophenethanol, 4-aminophen-ethanol, 2,3-diaminophenol, 4-aminoresorcinol, 2,4-diaminophenol, 1-amino-2-naphthol, 2-amino-1-phenylethanol, 2-phenylglycinol, norephedrine, pseudoephedrine, ephedrine, 2-amino-1-phenyl-1,3-propanediol, S-benzyl-L-cysteinol, tyramine, octopamine, synephrine, thiomicamine, 3,4-dihydroxybenzyl-amine, epinephrine, dopamine, propranolol, tyrosine, dopa, 3-phenylserine, dops, and phenyl-4-amino-salicylate; useful heterocyclic amino alcohols include: 4-hydroxy-methylimidazole, 4-hydroxy-indole, 1-indole-methanol, tryptophol, homotryptophol, serotonin, 5-hydroxy-tryptophan, 2,3-dihydroxypyridine, 2,6-pyridinedimethanol, and pyridoxine.

Polyols

Examples of polyols bearing alkane, and cycloalkane groups include: ethylene glycol, 1,3-propane, 1,2-propane, 2,3-butane, 1,5-pentane, 2,4-pentane, 3,3-dimethyl-1,2-butane, 1,6-hexane, 2,5-hexane, 2-ethyl-1,3-hexane, 1,8-octane, 1,2-octane, 1,10-decane, 1,2-decane, 1,14-tetradecane, 1,2-tetradecane and 1,16-hexadecane-diol; glycerol, 1,1,1-tris-(hydroxymethyl)-ethane, 1,2,3-heptane-triol, pentaerythritol (PE), threitol, erythritol, xylitol, ribose, fructose, glucose, 1,2-cyclopentane, 1,2-cyclohexanediol; 1,3,5-cyclohexanetriol, 1,2-cyclohexane-dimethanol, 1,2-cycloocatanediol, pinanediol, inositol and the following cascade polyols (CP-12 and CP-36) as taught in U.S. Pat. No. 4,587,329, the disclosure of which is hereby incorporated herein by reference.

Useful substituted polyols include: 3-methoxy-1,2-propanediol, diethylene glycol, dipropylene glycol, batyl alcohol, triethylene glycol, tripropylene glycol, tetraethylene glycol, pentaethylene glycol, hexaethylene glycol, dipentaerythritol, tripenterythritol, 1,2-dithiane-4,5-diol, 1,5-dithiacyclooctan-3-ol, 1,5,9,13,-tetrathiacyclohexadecane-3,11-diol, and 1,5,9,13,17,21-hexathia-cyclotetracosane-3,11,19-triol; gluconic acid, tartaric acid, mucic acid, quinic acid, shikimic acid, and ascorbic acid.

Other useful polyols are those wherein the hydroxy or hydroxyalkyl groups are attached to a homocycle or a heterocycle. Examples of polyols containing homocyclic and heterocyclic groups, and cyclic groups with substituents include: catechol, 4-t-butylcatechol, pyrogallol, resorcinol, olivetol, 2,3-dihydroxy-naphthalene, 4-t-butylcalix-(6)-arene, 1,3-benzenedimethanol, 1-phenyl-1,2-ethanediol, 2-benzyloxy-1,3-propanediol, 3-hydroxyphenethanol, hydro-quinone bis-(2-hydroxyethyl)ether, 4,4'-thio-diphenol, 2,4-dihydroxypropiophenone, phloretin, quinalizarin, purpurin, fisetin, myricetin, 3,5-dihydroxybenzoic acid, gallic acid, and resorcinol sulfoxide; polyol containing heterocycles include: 2,5-furandimethanol, and 2,5-thiophenedimethanol.

Other useful nucleophiles include dithiocarbamates. Specific examples of compounds from which such nucleophiles can be formed include but are not limited to the following: sodium diethyldithiocarbamate, sodium dithiocarbamate, sodium N-methyl dithiocarbamate, sodium dimethylcarbamate, sodium N-ethyl dithiocarbamate, and the like.

Utility of the Compounds of the Invention

The disclosed compounds may be used to treat conditions mediated directly by the proteolytic function of the proteasome such as muscle wasting, or mediated indirectly via proteins which are processed by the proteasome such as NF-kappaB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include beta-amyloid protein and regulatory proteins such as cyclins and transcription factor NF-kappaB. Treating as used herein includes reversing, reducing, or arresting the symptoms, clinical signs, and underlying pathology of a condition in manner to improve or stabilize the subject's condition.

Alzheimer's disease is characterized by extracellular deposits of beta-amyloid protein (beta-AP) in senile plaques and cerebral vessels. beta-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the beta-AP sequence, thereby preventing the generation of beta-AP. It is believed that abnormal protein processing by the proteasome contributes to the abundance of beta-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the beta-subunit of human macropain. Kojima, S. et al., Fed. Eur. Biochem. Soc., 1992, 304, 57-60. The APP-processing enzyme cleaves at the Gln15-Lys16 bond; in the presence of calcium ion, the enzyme also cleaves at the Met-1-Asp 1 bond, and the Asp1-Ala2 bonds to release the extracellular domain of beta-AP.

One embodiment, therefore, is a method of treating Alzheimer's disease, including administering to a subject an effective amount of a compound (e.g., pharmaceutical composition) having a formula disclosed herein. Such treatment includes reducing the rate of beta-AP processing, reducing the rate of beta-AP plaque formation, and reducing the rate of beta-AP generation, and reducing the clinical signs of Alzheimer's disease.

Other embodiments of the invention relate to methods of treating cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Proteasome inhibitors are useful for treating conditions such as cancer, chronic infectious diseases, fever, muscle disuse (atrophy) and denervation, nerve injury, fasting, renal failure associated with acidosis, and hepatic failure. See, e.g., U.S. Pat. No. 5,340,736, the disclosure of which is hereby incorporated herein by reference.

Additional embodiments of the invention therefore encompass methods of, reducing the rate of muscle protein degradation in a cell; reducing the rate of intracellular protein degradation; reducing the rate of degradation of p53 protein in a cell; and inhibiting the growth of p53 related cancers.

Each of these methods includes the step of contacting a cell (in vivo or in vitro, e.g., a muscle in a subject) with an effective amount of a compound (e.g., pharmaceutical composition) of a formula disclosed herein.

Another protein processed by the proteasome is NF-kappaB, a member of the Rel protein family. The Rel family of transcriptional activator proteins can be divided into two groups. The first group requires proteolytic processing, and includes p50 (NF-kappaB1, 105 kDa) and p52 (NF-kappa2, 100 kDa). The second group does not require proteolytic processing, and includes p65 (RelA, Rel (c-Rel), and RelB). Both homo- and heterodimers can be formed by Rel family members; NF-kappaB, for example, is a p50-p65 heterodimer. After phosphorylation and ubiquitination of IkappaB and p105, the two proteins are degraded and processed, respectively, to produce active NF-kappaB which translocates from the cytoplasm to the nucleus. Ubiquitinated p105 is also processed by purified proteasomes. Palombella et al., Cell 1994, 78, 773-785. Active NF-kappaB forms a stereospecific enhancer complex with other transcriptional activators and, e.g., HMG I(Y), inducing selective expression of a particular gene.

NF-kappaB regulates genes involved in the immune and inflammatory response, and mitotic events. For example, NF-kappaB is required for the expression of the immunoglobulin light chain kappa gene, the IL-2 receptor alpha-chain gene, the class I major histocompatibility complex gene, and a number of cytokine genes encoding, for example, IL-2, IL-6, granulocyte colony-stimulating factor, and IFN-beta. Palombella et al., supra. Some embodiments of the invention include methods of affecting the level of expression of IL-2, MHC-I, IL-6, IFN-beta or any of the other previously-mentioned proteins, each method including administering to a subject an effective amount of a compound of a formula disclosed herein.

NF-kappaB also participates in the expression of the cell adhesion genes that encode E-selectin, P-selectin, ICAm, and VCAM-1, Collins, T., Lab. Invest., 1993, 68, 499-508. One embodiment of the invention is a method of inhibiting cell adhesion (e.g., cell adhesion mediated by E-selectin, P-selectin, ICAm, or VCAM-1), including contacting a cell with (or administering to a subject) an effective amount of a compound (e.g., pharmaceutical composition) having a formula disclosed herein.

NF-kappaB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of 1-kappaB, triggering IkappaB degradation through the ubiquitin-proteasome pathway. After degradation, NF-kappaB is released into the nucleus, thus enhancing the transcription of HIV. Cohen, J., Science, 1995, 267, 960. Additional embodiments of the invention are a method of inhibiting or reducing HIV infection in a subject, and a method of decreasing the level of viral gene expression, each method including administering to the subject an effective amount of a compound of a formula disclosed herein.

Complexes including p50 are rapid mediators of acute inflammatory and immune responses. Thanos et al., Cell, 1995, 80, 529-532. Intracellular proteolysis generates small peptides for presentation to T-lymphocytes to induce MHC class I-mediated immune responses. The immune system screens for autologous cells that are virally infected or have undergone oncogenic transformation. Additional embodiments of the invention are a method of inhibiting antigen presentation in a cell, including exposing the cell to a compound of a formula described herein, and a method of suppressing the immune system of a subject (e.g., inhibiting transplant rejection), including administering to the subject an effective amount of a compound of a formula described herein.

In addition, the invention provides a method of treating inflammation, wherein the method includes administering to a subject an effective anti-inflammatory amount of a pharmaceutical composition containing a compound of a formula described herein. Inflammation can be a primary or secondary response associated with (a) injury such as a cut, laceration, puncture wound, (b) infection (including infected surgical incisions) by one or more viruses, bacteria, mycobacteria, microorganisms, parasites, and fungi, (c) allergies, (d) a disease state, (e) surgery (e.g., transplantation), or (f) a combination thereof.

Allergies are primary inflammatory responses to antigens or allergens. Sources of allergens include plants (e.g., grass or tree pollen), animals (e.g., dander, venom, urine, execreta from dogs, cats, insects, and snakes), and fungi. In addition to allergens such as rye grass, ragweed, and Japanese cedar pollen, certain foods or food components (e.g., eggs, milk, shellfish, strawberries, chocolate), vaccines, and drugs (e.g., penicillin) can induce allergic reactions in certain individuals.

Disease states include rheumatoid arthritis, scleroderma, rheumatic fever, inflammatory bowel disease (e.g., Crohn's disease and ulcerative colitis), diabetes mellitus, myasthenia gravis, multiple sclerosis, Guillain-Barre syndrome, conjunctiva of the eye, systemic lupus erythematosus, encephalitis, Adult Respiratory Distress Syndrome, psoriasis, emphysema, Alzheimer's disease, and muscular dystrophy.

The invention provides a method of treating inflammation induced by organ or tissue transplantation. This method includes administering to a patient who has undergone or is about to undergo transplantation a composition containing a compound having a formula disclosed herein. Transplantations include bone marrow, solid organ (e.g., kidney, lungs, heart, pancreas, liver, and skin), or tissues.

Certain proteasome inhibitors block both degradation and processing of ubiquitinated NF-kappaB in vitro and in vivo. Proteasome inhibitors also block IkappaB-alpha degradation and NF-kappaB activation, Palombella et al.; and Traenckner et al., EMBO J., 1994, 13, 5433-5441. One embodiment of the invention is a method of inhibiting IkappaB-alpha degradation, including contacting the cell with a compound of a formula described herein. A further embodiment is a method of reducing the cellular content of NF-kappaB in a cell, muscle, organ, or subject, including contacting the cell, muscle, organ, or subject with a compound of a formula described herein.

Proteasome inhibitors are also useful for treatment of ischemic or reperfusion injury, particularly for preventing or reducing the size of infarct after vascular occlusion such as occurs during a stroke or heart attack, as described in U.S. Pat. No. 6,271,199, the disclosure of which is hereby incorporated herein by reference. Proteasome inhibitors also block proteasome-dependent transformation of protozoan parasites (Gonzalez et al., J. Exp. Med., 1996, 84, 1909. Further embodiments of the invention therefore encompass methods for treating an infarct or a protozoan parasitic disease by administering a compound of a formula disclosed herein. In a preferred aspect of the invention, a compound of the present invention is administered to prevent or reduce the size of the infarct after vascular occlusion. Said compounds can be administered from about 0 to about 10 hours from the occurrence of a stroke in order to treat or reduce neuronal loss following an ischemic event.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Other embodiments of the invention are methods for affecting cyclin-dependent eukaryotic cell cycles, including exposing a cell (in vitro or in vivo) to a compound of a formula disclosed herein. Cyclins are proteins involved in cell cycle control. The proteasome participates in the degradation of cyclins. Examples of cyclins include mitotic cyclins, G1 cyclins, (cyclin B). Degradation of cyclins enables a cell to exit one cell cycle stage (e.g., mitosis) and enter another (e.g., division). It is believed all cyclins are associated with p34cdc2 protein kinase or related kinases. The proteolysis targeting signal is localized to amino acids 42-RAALGN-ISEN-50 (destruction box). There is evidence that cyclin is converted to a form vulnerable to a ubiquitin ligase or that a cyclin-specific ligase is activated during mitosis. Ciechanover, A., Cell, 1994, 79, 13-21. Inhibition of the proteasome inhibits cyclin degradation, and therefore inhibits cell proliferation (e.g., cyclin-related cancers). Kumatori et al., Proc. Natl. Acad. Sci. USA, 1990, 87, 7071-7075. One embodiment of the invention is a method of treating a proliferative disease in a subject (e.g., cancer, psoriasis, or restenosis), including administering to the subject an effective amount of a compound of a formula disclosed herein. Chronic or acute inflammation can result from transplantation rejection, arthritis, rheumatoid arthritis, infection, dermatosis, inflammatory bowel disease, asthma, osteoporosis, and autoimmune diseases. Rejection or inflammation can occur in transplanted tissues or organs of any type, including heart, lung, kidney, liver, skin grafts, and tissue grafts. The invention also encompasses a method of treating cyclin-related inflammation in a subject, including administering to a subject an effective amount of a compound of a formula described herein.

Additional embodiments are methods for affecting the proteasome-dependent regulation of oncoproteins and methods of treating or inhibiting cancer growth, each method including exposing a cell (in vivo, e.g., in a subject or in vitro) to a compound of a formula disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method of treating p53-related apoptosis, including administering to a subject an effective amount of a compound of a formula disclosed herein.

Treatment of cancer prevents, alleviates, or ameliorates one or more primary or secondary phenomena associated with the initiation, progression, and metastasis of tumors, especially malignant tumors, e.g., a growth of tissue wherein cell multiplication is uncontrolled. Malignant tumors show a greater degree of anaplasia than do benign tumors. The invention provides a method of treating cancer including administering to a subject an effective anti-cancer amount of a pharmaceutical composition described herein, wherein the cancer is selected from carcinoma, lymphoma, sarcoma, and myeloma.

Examples of carcinomas include adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Examples of sarcomas include amelioblastic sarcoma, angiolithic sarcoma, botryoid sarcoma, endometrial stroma sarcoma, ewing sarcoma, fascicular sarcoma, giant cell sarcoma, granulocytic sarcoma, immunoblastic sarcoma, juxaccordial osteogenic sarcoma, coppices sarcoma, leukocytic sarcoma (also known as leukemia), lymphatic sarcoma (also known as lympho sarcoma), medullary sarcoma, myeloid sarcoma (also known as granulocytic sarcoma), osteogenic sarcoma, periosteal sarcoma, reticulum cell sarcoma (also known as histiocytic lymphoma), round cell sarcoma, spindle cell sarcoma, synovial sarcoma, and telangiectatic audiogenic sarcoma. Examples of lymphomas include Hodgkin's disease and lymphocytic lymphomas, such as Burkitt's, nodular poorly-differentiated lymphocytic (NPDL), nodular mixed lymphocytic (NML), NH (nodular histiocytic), and diffuse lymphomas. Additional carcinomas include neural blastoma, glioblastoma, astrocytoma, melanoma, leiomyo sarcoma, multiple myeloma, and Hemangioma.

A tripeptide aldehyde protease inhibitor (benzyloxycarbonyl (Z)-Leu-Leu-leucinal induces neurite outgrowth in PC12 cells at an optimal concentration of 30 nM, Tsubuki et al., Biochem. and Biophys. Res. Comm., 1993, 196, 1195-1201. Peptide aldehydes have been shown to inhibit the chymotryptic activity of the proteasome. Vinitsky et al., 1992, Tsubuki et al., 1993. One embodiment of the invention is a method of promoting neurite outgrowth, including administering to the subject a compound of a formula disclosed herein.

Finally, the disclosed compounds are also useful as diagnostic agents (e.g., in diagnostic kits or for use in clinical laboratories) for screening for proteins (e.g., enzymes, transcription factors) processed by the proteasome. The disclosed compounds are also useful as research reagents for specifically binding the X/MB1 subunit or alpha-chain and inhibiting the proteolytic activities associated with it. For example, the activity of (and specific inhibitors of) other subunits of the proteasome can be determined.

Most cellular proteins are subject to proteolytic processing during maturation or activation. The compounds of the invention can be used to determine whether a cellular, developmental, or physiological process or output is regulated by the proteolytic activity of the proteasome. One such method includes obtaining an organism, an intact cell preparation, or a cell extract; exposing the organism, cell preparation, or cell extract to a compound of a formula disclosed herein; exposing the compound-exposed organism, cell preparation, or cell extract to a signal, and monitoring the process or output. The high selectivity of the compounds disclosed herein permits rapid and accurate elimination or implication of the proteasome in a given cellular, developmental, or physiological process.

Formulation and Administration

The methods of the invention contemplate treatment of animal subjects, such as mammals (e.g., higher primates, and especially humans). The invention encompasses pharmaceutical compositions which include novel compounds described herein, and pharmaceutical compositions which include compounds described and recognized herein as proteasome inhibitors.

Pharmaceutically acceptable salts may be formed, for example, with 1, 2, 3, or more equivalents of hydrogen chloride, hydrogen bromide, trifluoroacetic acid, and others known to those in the art of drug formulation. Compounds of the invention can be formulated into pharmaceutical compositions by admixture with pharmaceutically acceptable non-toxic excipients and carriers. A pharmaceutical composition of the invention may contain more than one compound of the invention, and/or may also contain other therapeutic compounds not encompassed by the invention, such as anti-inflammatory, anti-cancer, or other agents. A subject may have more than one type of inflammation, or more than one type of cancer, a combination of allergies, or a mixture of the above conditions for which the disclosed compounds are useful. A compound of the invention may be administered in unit dosage form, and may be prepared by any of the methods well known in the pharmaceutical art, for example, as described in Remington's Pharmaceutical Sciences (Mack Pub. Co., Easton, Pa., 1980). The invention also encompasses a packaged drug, containing a pharmaceutical composition formulated into individual dosages and printed instructions for self-administration.

Compounds disclosed herein as proteasome inhibitors may be prepared for use in parenteral administration in the form of solutions or liquid suspensions; for oral administration (preferable), particularly in the form of tablets or capsules; or intranasally, particularly in the form of powders, gels, oily solutions, nasal drops, aerosols, or mists. Formulations for parenteral administration may contain as common excipients sterile water or sterile saline, polyalkylene glycols such as polyethylene glycol, oils of vegetable origin, hydrogenated naphthalenes, and the like. Controlled release of a compound of the invention may be obtained, in part, by use of biocompatible, biodegradable polymers of lactide, and copolymers of lactide/glycolide or polyoxyethylene/polyoxypropylene. Additional parental delivery systems include ethylene-vinyl acetate copolymer particles, osmotic pumps, implantable infusion systems, and liposomes. Formulations for inhalation administration contain lactose, polyoxyethylene-9-lauryl ether, glycocholate, or deoxycholate. Formulations for buccal administration may include glycocholate; formulations for vaginal administration may include citric acid.

The concentration of a disclosed compound in a pharmaceutically acceptable mixture will vary depending on several factors, including the dosage of the compound to be administered, the pharmacokinetic characteristics of the compound(s) employed, and the route of administration. In general, the compounds of this invention may be provided in an aqueous physiological buffer solution containing about 0.1-10% w/v of compound for parenteral administration. Typical dose ranges are from about 0.1 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

The effective amount of the active compound used to practice the present invention for treatment of conditions directly or indirectly mediated by the proteasome varies depending upon the manner of administration, the age and the body weight of the subject and the condition of the subject to be treated, and ultimately will be decided by the attending physician or veterinarian. Such amount of the active compound as determined by the attending physician or veterinarian is referred to herein as "effective amount."

EXAMPLES

General Procedures. All reactions were performed in oven- or flame-dried round bottomed or modified Schlenk flasks fitted with rubber septa under a positive pressure of argon, unless otherwise noted. Air- and moisture-sensitive liquids and solutions were transferred via syringe or stainless steel cannula. Where necessary (so noted), solutions were deoxygenated by alternative freeze (liquid nitrogen)/evacuation/thaw cycles ($\geq$three iterations). Organic solutions were concentrated by rotary evaporation (house vacuum, ~25 Torr) at 23-30° C. Flash column chromatography was performed as described by Still et al.,[1] employing silica gel (60-Å pore size, 230-400 mesh, Merck KGA; or 60-Å pore size, 32-63 µm, standard grade, Sorbent Technologies). Analytical thin-layer chromatography (TLC) was performed using glass plates pre-coated with silica gel (0.25 mm, 60-Å pore size, 230-400 mesh, Merck KGA) impregnated with a fluorescent indicator (254 nm). TLC plates were visualized by exposure to ultraviolet light (UV) and/or exposure to ceric ammonium molybdate solution (CAM), ethanolic phosphomolybdic acid (PMA), or an acidic solution of p-anisaldehyde (anisaldehyde) followed by brief heating on a hot plate (~200° C., 10-15 s).

(1) Still, W. C.; Kahn, M.; Mitra, A. *J. Org. Chem.* 1978, 43, 2923.

Materials. Commercial reagents and solvents were used as received unless mentioned otherwise. Dichloromethane, ether, tetrahydrofuran, N,N-dimethylformamide and toluene were purified by the method of Pangborn et al.[2] The molarity of solutions of n-butyllithium was determined by titration against a standard solution of diphenylacetic acid in tetrahydrofuran (average of three determinations).[3]

(2) Pangborn, A. B.; Giardello, M. A.; Grubbs, R. H.; Rosen, R. K.; Timmers, F. J. *Organometallics* 1996, 15, 1518.

(3) Kofron, W. G.; Baclawski, L. M. *J. Org. Chem.* 1976, 41, 1879.

Instrumentation. Proton nuclear magnetic resonance ($^1$H NMR) spectra and carbon nuclear magnetic resonance ($^{13}$C NMR) were recorded with Varian Unity/Inova 600 (600 MHz), Varian Unity/Inova 500 (500 MHz/125 MHz), or Varian Mercury 400 (400 MHz/100 MHz) NMR spectrometers. Chemical shifts for protons are reported in parts per million scale (δ scale) downfield from tetramethylsilane and are referenced to residual protium in the NMR solvents (CHCl$_3$: δ 7.26). Chemical shifts for carbon are reported in parts per million (δ scale) downfield from tetramethylsilane and are referenced to the carbon resonances of the solvent (CDCl$_3$: δ 77.0). Data are represented as follows: chemical shift, multiplicity (s=singlet, d=doublet, t=triplet, q=quartet, m=multiplet, br=broad), integration, coupling constant in Hz, and assignment. Infrared (IR) spectra were obtained using a Perkin-Elmer 1600 FT-IR spectrophotometer referenced to a polystyrene standard. High resolution mass spectra were obtained at the Harvard University Mass Spectrometry Facilities. Crystallographic analysis was performed at the Harvard University x-ray Crystallography Laboratory.

Reaction Scheme IV: Synthetis of racemic (±)-7,8-dihydrosalinosporamide

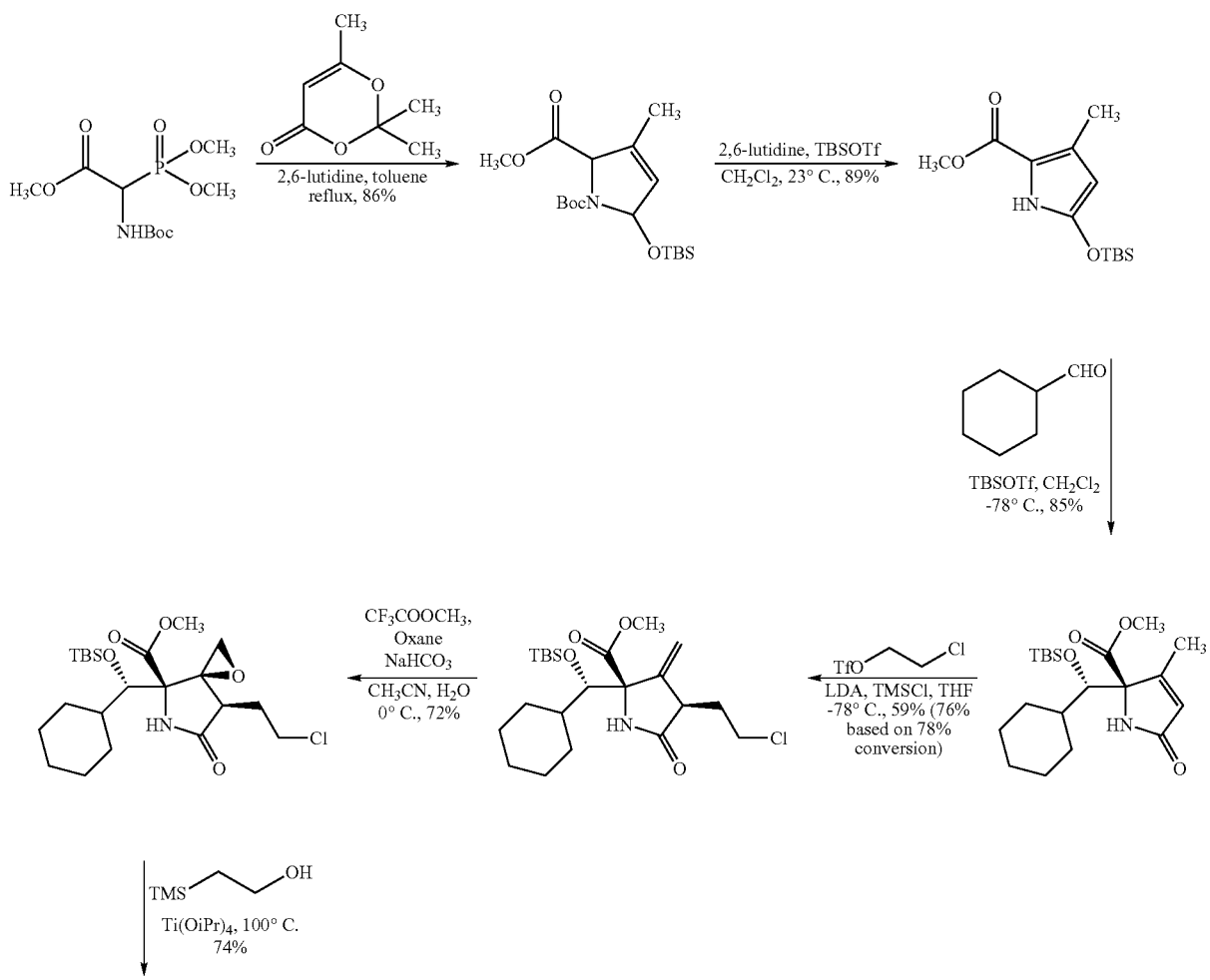

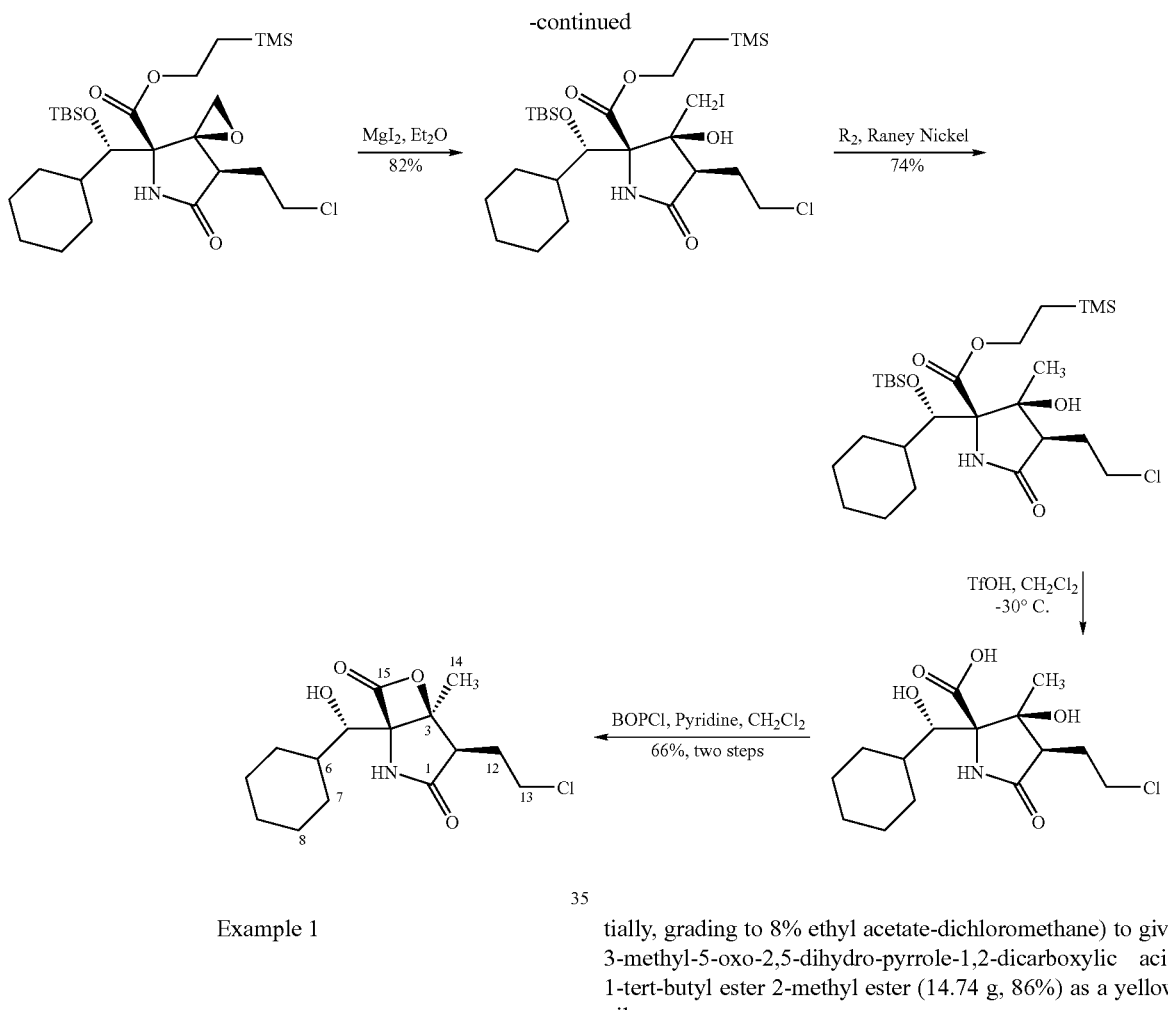

Example 1

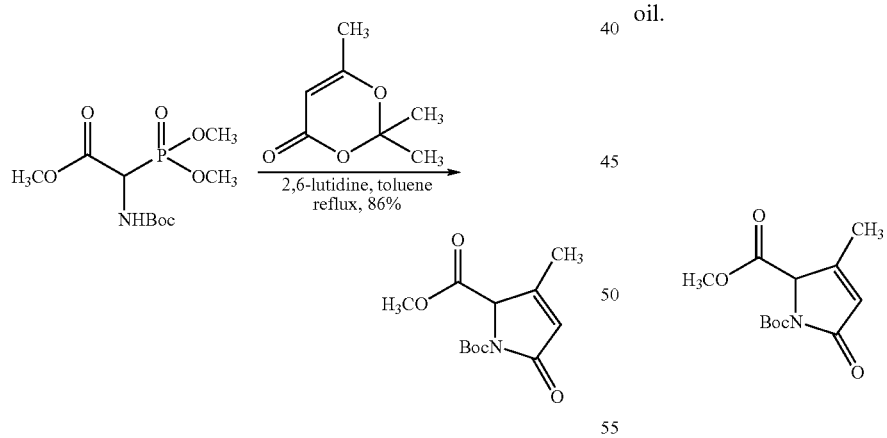

3-Methyl-5-oxo-2,5-dihydro-pyrrole-1,2-dicarboxylic acid 1-tert-butyl ester 2-methyl ester A solution of tert-butoxycarbonylamino-(dimethoxyphosphoryl)-acetic acid methyl ester (20.0 g, 67 mmol, 1 equiv), 2,2,6-trimethyl-[1,3]dioxin-4-one (43.96 ml, 47.8 g, 336 mmol, 5.0 equiv), and 2,6-lutidine (11.71 ml, 10.77 g, 101 mmol, 1.5 equiv) in toluene (200 ml) was heated at reflux for 16 h. The reaction mixture was allowed to cool to 23° C. and was concentrated. The residue was purified by flash column chromatography (5% ethyl acetate-dichloromethane initially, grading to 8% ethyl acetate-dichloromethane) to give 3-methyl-5-oxo-2,5-dihydro-pyrrole-1,2-dicarboxylic acid 1-tert-butyl ester 2-methyl ester (14.74 g, 86%) as a yellow oil.

$^1$H NMR (500 MHz, CDCl$_3$)δ: 5.92 (s, 1 H, CHC(O)OCH$_3$), 4.94 (s, 1 H, CHC(O)N), 3.79 (s, 3 H, CHC(O)OCH$_3$), 2.06 (s, 3 H, CH$_3$CCHC(O)N), 1.50 (s, 9 H, (CH$_3$)$_3$COC(O)N) $^{13}$C NMR (100 MHz, CDCl$_3$)δ: 168.4, 167.4, 154.8, 148.3, 124.2, 83.4, 66.9, 52.9, 27.9, 14.6 HRMS (ESI$^+$): m/z calcd for (C$_{12}$H$_{18}$NO$_5$)$^+$ 256.1185, found: 256.1191. FTIR (cm$^{-1}$): 2976, 1788, 1747, 1710, 1643

Example 2

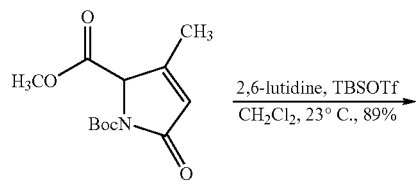

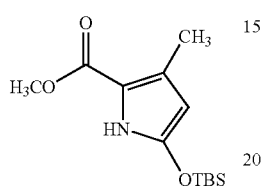

5-(tert-Butyl-dimethyl-silanyloxy)-3-methyl-1H-pyrrole-2-carboxylic acid methyl ester tert-Butyldimethylsilyltrifluoromethanesulfonate (9.99 ml, 11.49 g, 43.5 mmol, 3.0 equiv) was added to a stirring solution of 3-methyl-5-oxo-2,5-dihydro-pyrrole-1,2-dicarboxylic acid 1-tert-butyl ester 2-methyl ester (3.7 g, 14.5 mmol, 1.0 equiv) and 2,6-lutidine (5.07 ml, 4.66 g, 43.5 mmol, 3.0 equiv) in dichloromethane (100 ml) at 23° C. The mixture was stirred at 23° C. for 15 h, then washed with pH=7 buffer solution (30 ml). The aqueous layer was extracted with two 40 ml portions of dichloromethane. The combined organic layers were dried over sodium sulfate. The solids were filtered and the filtrate was concentrated. The residue was purified by flash column chromatography (3% ethyl acetate-hexanes initially, grading to 6% ethyl acetate-hexanes) to afford 5-(tert-Butyl-dimethyl-silanyloxy)-3-methyl-1H-pyrrole-2-carboxylic acid methyl ester (3.46 g, 89%) as a yellow oil.

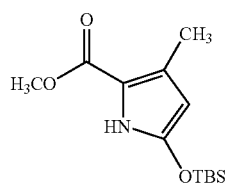

$^1$H NMR (500 MHz, CDCl$_3$)δ: 8.09 (br. s, 1 H, NH), 5.20 (s, 1 H, CHC(NH)OTBS), 3.79 (s, 3H, CHC(O)OCH$_3$), 2.28 (s, 3 H, CH$_3$CCHCOTBS), 0.96 (s, 9 H, (CH$_3$)$_3$CSi), 0.23 (s, 6H, (CH$_3$)$_2$Si) $^{13}$C NMR (100 MHz, CDCl$_3$)δ: 162.1, 145.5, 129.9, 110.0, 95.4, 50.9, 25.7, 18.3, 13.5, −4.6 HRMS (ESI$^+$):

m/z calcd for (C$_{13}$H$_{24}$NO$_3$Si)$^+$ 270.1525, found: 270.1524. FTIR (cm$^{-1}$): 3290, 2953, 2856, 1674, 1581, 1511

Example 3

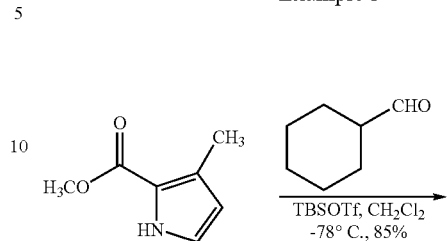

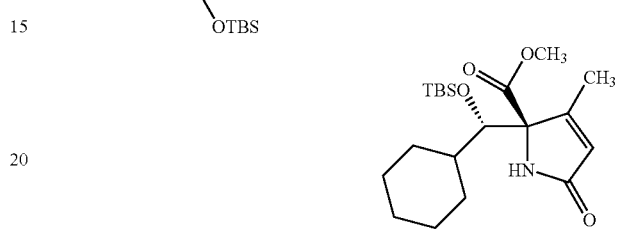

2-[(tert-Butyl-dimethyl-silanyloxy)-cyclohexyl-methyl]-3-methyl-5-oxo-2,5-dihydro-1H-pyrrole-2-carboxylic acid methyl ester tert-Butyldimethylsilyltrifluoromethanesulfonate (2.40 ml, 2.75 g, 10.4 mmol, 2.0 equiv) was added dropwise over 8 min to a stirring solution of 5-(tert-butyl-dimethyl-silanyloxy)-3-methyl-1H-pyrrole-2-carboxylic acid methyl ester (1.4 g, 5.2 mmol, 1.0 equiv) and cyclohexanecarbaldehyde (0.94 ml, 0.87 g, 7.8 mmol, 1.5 equiv) in dichloromethane (100 ml) at −78° C. The resultant solution was stirred at −78° C. for 2 h, then pH=7 buffer solution (50 ml) was added. The organic layer was washed with brine solution (50 ml), and dried over sodium sulfate. The solids were filtered and the filtrate was concentrated. The residue obtained was purified by flash column chromatography (5% ethyl acetate-dichloromethane initially, grading to 8% ethyl acetate-dichloromethane, then to 10% ethyl acetate-dichloromethane) to give 2-[(tert-butyl-dimethyl-silanyloxy)-cyclohexyl-methyl]-3-methyl-5-oxo-2,5-dihydro-1H-pyrrole-2-carboxylic acid methyl ester (1.69 g, 85%) as a colorless oil.

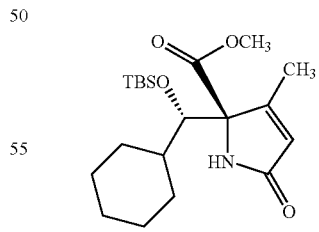

$^1$H NMR (500 MHz, CDCl$_3$)δ: 6.48 (br. s, 1 H, NH), 5.82 (s, 1 H, CHC(O)NH), 4.19 (s, 1 H, CHOTBS), 3.72 (s, 3 H, C(O)OCH$_3$), 2.17 (s, 3H, CH$_3$CCHC(O)NH), 1.03-1.73 (m, 11 H, cyclohexyl), 0.85 (s, 9 H, (CH$_3$)$_3$CSi), 0.11 (s, 3H, CH$_3$Si), −0.01 (s, 3H, CH$_3$Si) $^{13}$C NMR (100 MHz, CDCl$_3$)δ: 173.2, 169.7, 160.0, 125.0, 78.3, 75.2, 52.8, 40.4, 31.9, 27.8, 26.8, 26.4, 26.0, 25.9, 18.4, 16.3, −3.5, −4.7 HRMS (ESI$^+$):

m/z calcd for $(C_{20}H_{36}NO_4Si)^+$ 382.2413, found: 382.2405. FTIR (cm$^{-1}$): 2928, 2854, 1744, 1701

Example 4

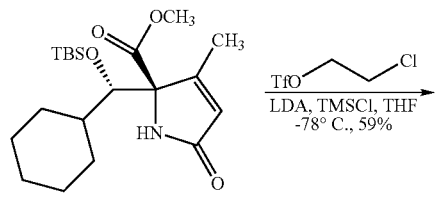

2-[(tert-Butyl-dimethyl-silanyloxy)-cyclohexyl-methyl]-4-(2-chloro-ethyl)-3-methylene-5-oxo-pyrrolidine-2-carboxylic acid methyl ester Lithium diisopropylamide solution (0.67 M solution in tetrahydrofuran, 0.09 ml, 0.06 mmol, 1.0 equiv) was added dropwise via syringe to a stirred solution of 2-[(tert-butyl-dimethyl-silanyloxy)-cyclohexyl-methyl]-3-methyl-5-oxo-2,5-dihydro-1H-pyrrole-2-carboxylic acid methyl ester (23 mg, 0.06 mmol, 1.0 equiv) in tetrahydrofuran (1.5 ml) at −78° C. The reaction mixture was stirred at −78° C. for 30 min. Chlorotrimethylsilane (8 μl, 6.8 mg, 0.06 mmol, 1.0 equiv) was added and the resultant solution was stirred at −78° C. for 2.5 h. Another equiv of lithium diisopropylamide solution (0.67 M solution in tetrahydrofuran, 0.09 ml, 0.06 mmol, 1.0 equiv) was added dropwise at −78° C. The reaction mixture was stirred −78° C. for 30 min. A stock solution of trifluoromethanesulfonic acid 2-chloro-ethyl ester in toluene (2.45 M, 0.1 ml, 0.24 mmol, 4.0 equiv) was added dropwise via syringe at −78° C. The reaction mixture was stirred at −78° C. for 50 min. A buffer solution (pH=7, 5 ml) was added at −78° C. The organic layer was separated, washed with brine solution (5 ml), dried over sodium sulfate and the solids were filtered. The filtrate was concentrated. The residue was purified by flash column chromatography (10% ethyl acetate-hexanes initially, grading to 20% ethyl acetate-hexanes) to furnish 2-[(tert-butyl-dimethyl-silanyloxy)-cyclohexyl-methyl]-4-(2-chloro-ethyl)-3-methylene-5-oxo-pyrrolidine-2-carboxylic acid methyl ester (16 mg, 59%) along with recovered starting material (5 mg, 22%).

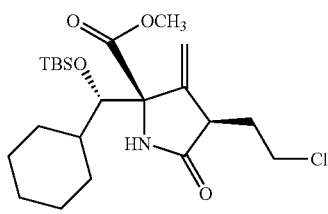

$^1$H NMR (500 MHz, CDCl$_3$)δ: 6.18 (br. s, 1 H, NH), 5.67 (d, 1 H, J=2.0 Hz, CH$_2$CCHC(O)NH), 5.22 (d, 1 H, J=2.4 Hz, CH$_2$CCHC(O)NH), 4.05 (d, 1 H, J=2.9 Hz, CHOTBS), 3.74-3.79 (m, 1 H, CH$_2$Cl), 3.75 (s, 3 H, C(O)OCH$_3$), 3.59-3.64 (m, 1 H, CH$_2$Cl), 3.15-3.17 (m, 1 H, CHC(O)NH), 2.09-2.14 (m, 2 H, CH$_2$CH$_2$Cl), 1.06-1.75 (m, 11 H, cyclohexyl), 0.87 (s, 9 H, (CH$_3$)$_3$CSi), 0.08 (s, 3H, CH$_3$Si), −0.01 (s, 3H, CH$_3$Si)

$^{13}$C NMR (100 MHz, CDCl$_3$)δ: 176.6, 171.2, 145.9, 111.5, 80.7, 73.5, 52.7, 43.1, 42.7, 41.6, 34.2, 31.2, 28.8, 26.8, 26.4, 26.1, 26.0, 18.3, −3.9, −4.0 HRMS (ESI$^+$): m/z calcd for $(C_{22}H_{39}ClNO_4Si)^+$ 444.2337, found: 444.2336. FTIR (cm$^{-1}$): 3205, 3094, 2928, 2855, 1733, 1706, 1660

Example 5

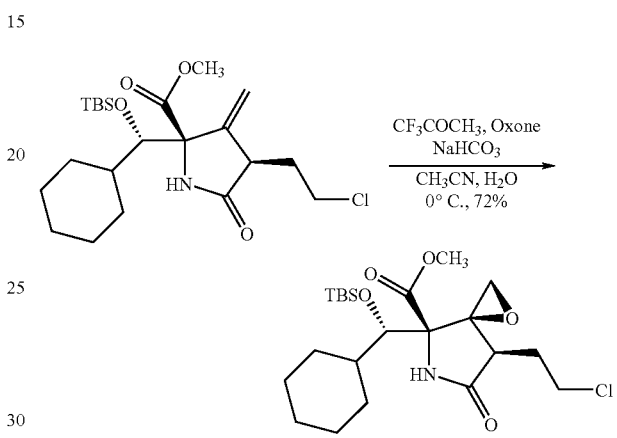

4-[(tert-Butyl-dimethyl-silanyloxy)-cyclohexyl-methyl]-7-(2-chloro-ethyl)-6-oxo-1-oxa-5-aza-spiro [2.4]heptane-4-carboxylic acid methyl ester.

An aqueous ethylenediaminetetraacetic acid disodium solution (1.04 ml, 4×10$^{-4}$ M) was added to a stirred solution of 2-[(tert-butyl-dimethyl-silanyloxy)-cyclohexyl-methyl]-4-(2-chloro-ethyl)-3-methylene-5-oxo-pyrrolidine-2-carboxylic acid methyl ester (71 mg, 0.16 mmol, 1.0 equiv) in acetonitrile (2.6 ml) and the reaction mixture was cooled to 0° C. Trifluoroacetone (0.6 ml) was added via a precooled syringe. A mixture of sodium bicarbonate (0.313 g, 3.72 mmol, 23.25 equiv) and Oxone (0.738 g, 1.2 mmol, 7.5 equiv) was added. The reaction mixture was stirred for 4 h at 0° C. Water (20 ml) was added and the resultant mixture was extracted with dichloromethane (100 ml). The organic layer was separated, dried over sodium sulfate and the solids were filtered. The filtrate was concentrated. Purification of the residue by flash column chromatography (15% ethyl acetate-hexanes initially, grading to 20% ethyl acetate-hexanes) provided 4-[(tert-butyl-dimethyl-silanyloxy)-cyclohexyl-methyl]-7-(2-chloro-ethyl)-6-oxo-1-oxa-5-aza-spiro[2.4] heptane-4-carboxylic acid methyl ester (53 mg, 72%).

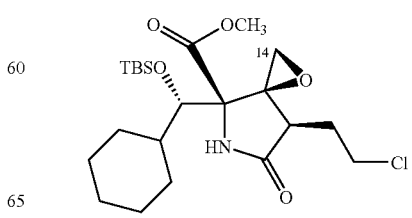

¹H NMR (500 MHz, CDCl₃)δ: 6.10 (s, 1 H, NH), 4.08 (d, 1 H, J=3.4 Hz, CHOTBS), 3.86-3.91 (m, 1 H, CH₂Cl), 3.72 (s, 3 H, C(O)OCH₃), 3.61-3.66 (m, 1 H, CH₂Cl), 3.21 (d, 1 H, J=3.9 Hz, C (14)-H), 3.18-3.21 (m, 1 H, CHC(O)NH), 2.86 (d, 1 H, J=3.9 Hz, C (14)-H), 1.95-2.02 (m, 1 H, CH₂CH₂Cl), 1.04-1.75 (m, 12 H, cyclohexyl, CH₂CH₂Cl), 0.92 (s, 9 H, (CH₃)₃CSi), 0.16 (s, 3 H, CH₃Si), 0.09 (s, 3 H, CH₃Si) ¹³C NMR (100 MHz, CDCl₃)δ: 176.3, 168.4, 78.5, 73.0, 64.4, 52.7, 46.4, 44.6, 43.1, 39.2, 30.7, 30.0, 28.2, 27.2, 27.1, 26.5, 26.3, 18.5, −3.3, −3.4 HRMS (ESI⁺): m/z calcd for $(C_{22}H_{39}ClNO_5Si)^+$ 460.2286, found: 460.2290. FTIR (cm⁻¹): 3202, 3097, 2931, 2856, 1706

Example 6

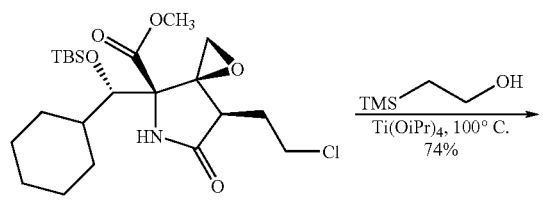

4-[(tert-Butyl-dimethyl-silanyloxy)-cyclohexyl-methyl]-7-(2-chloro-ethyl)-6-oxo-1-oxa-5-aza-spiro [2.4]heptane-4-carboxylic acid 2-trimethylsilanyl-ethyl ester.

Titanium (IV) isopropoxide (0.30 ml, 0.42 g, 1.5 mmol, 11.5 equiv) was added to a stirred solution of 4-[(tert-butyl-dimethyl-silanyloxy)-cyclohexyl-methyl]-7-(2-chloro-ethyl)-6-oxo-1-oxa-5-aza-spiro[2.4]heptane-4-carboxylic acid methyl ester (60 mg, 0.13 mmol, 1.0 equiv) in 2-trimethylsilanyl-ethanol (1.5 ml), and the resultant solution was heated at 100° C. for 17 h. The reaction mixture was allowed to cool to 23° C. and ethyl acetate (30 ml) and water (20 ml) was added. The resultant solution was stirred for 10 min and filtered through Celite. The organic layer was separated and the aqueous layer was extracted with ethyl acetate (15 ml×2). The combined organic layers were dried over sodium sulfate and the solids were filtered. The filtrate was concentrated. The residue was purified by flash column chromatography (10% ethyl acetate-hexanes initially, grading to 20% ethyl acetate-hexanes) to afford 4-[(tert-butyl-dimethyl-silanyloxy)-cyclohexyl-methyl]-7-(2-chloro-ethyl)-6-oxo-1-oxa-5-aza-spiro [2.4]heptane-4-carboxylic acid 2-trimethylsilanyl-ethyl ester (61 mg, 74%) as a colorless oil.

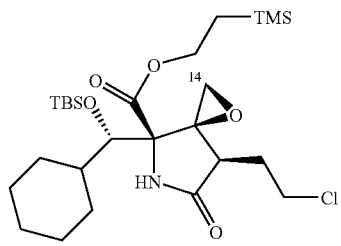

¹H NMR (500 MHz, CDCl₃)δ: 7.10 (s, 1 H, NH), 4.11-4.25 (m, 2 H, C(O)OCH₂CH₂Si), 4.06 (d, 1 H, J=2.0 Hz, CHOTBS), 3.84-3.88 (m, 1 H, CH₂Cl), 3.60-3.64 (m, 1 H, CH₂Cl), 3.18 (s, 1 H, C (14)-H), 3.16 (t, 1 H, J=6.6 Hz, CHC(O)NH), 2.82 (s, 1H, C (14)-H), 1.91-1.98 (m, 1H, CH₂CH₂Cl), 1.04-1.70 (m, 12 H, cyclohexyl, CH₂CH₂Cl), 1.00 (t, 2 H, J=9.3 Hz, CH₂CH₂Si), 0.90 (s, 9 H, (CH₃)₃CSi), 0.14 (s, 3 H, CH₃Si), 0.06 (s, 3 H, CH₃Si), 0.02 (s, 9 H, (CH₃)₃Si) ¹³C NMR (100 MHz, CDCl₃)δ: 176.5, 168.0, 78.7, 73.1, 64.5, 64.3, 46.3, 44.0, 43.1, 39.3, 31.0, 29.8, 28.3, 27.2, 26.9, 26.5, 26.4, 18.5, 17.5, −1.3, −3.1, −3.4 HRMS (ESI⁺): m/z calcd for $(C_{26}H_{49}ClNO_5Si_2)^+$ 546.2838, found: 546.2831. FTIR (cm⁻¹): 3188, 3097, 2929, 2857, 1706

Example 7

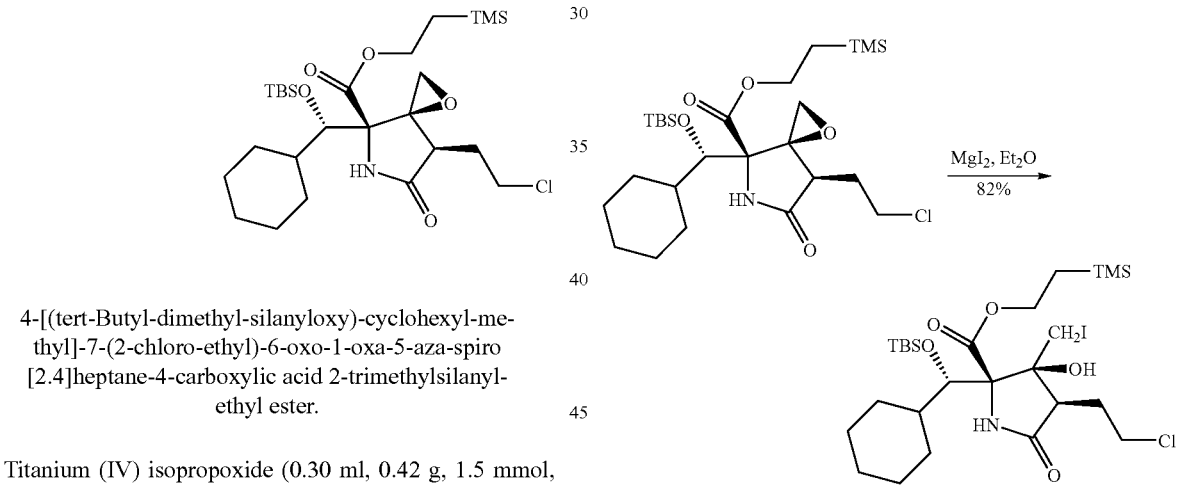

2-[(tert-Butyl-dimethyl-silanyloxy)-cyclohexyl-methyl]-4-(2-chloro-ethyl)-3-hydroxy-3-iodomethyl-5-oxo-pyrrolidine-2-carboxylic acid 2-trimethylsilanyl-ethyl ester Magnesium iodide (102 mg, 0.37 mmol, 2.0 equiv) was added to a solution of 4-[(tert-butyl-dimethyl-silanyloxy)-cyclohexyl-methyl]-7-(2-chloro-ethyl)-6-oxo-1-oxa-5-aza-spiro[2.4]heptane-4-carboxylic acid 2-trimethylsilanyl-ethyl ester (100 mg, 0.18 mmol, 1.0 equiv) in ether (10 ml) at 0° C. The reaction mixture was stirred at 0° C. for 1 h, then warmed to 23° C., and stirred at 23° C. for 3 h. The reaction solution was diluted with ethyl acetate (50 ml), and washed with brine solution (10 ml). The organic layer was separated, dried over sodium sulfate and the solids were filtered. The filtrate was concentrated. The residue was purified by flash column chromatography (10% ethyl acetate-hexanes) to afford 2-[(tertbutyl-dimethyl-silanyloxy)-cyclohexyl-methyl]-4-(2-chloro-ethyl)-3-hydroxy-3-iodomethyl-5-oxo-pyrrolidine-2-carboxylic acid 2-trimethyl-silanyl-ethyl ester (101 mg, 82%).

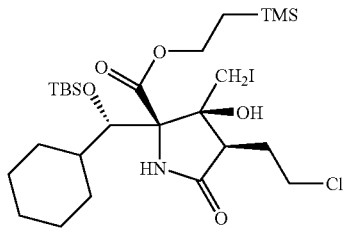

$^1$H NMR (500 MHz, CDCl$_3$)δ: 8.14 (br. s, 1 H, NH), 5.73 (br. s, 1 H, OH), 4.30-4.36 (m, 1 H, C(O)OCH$_2$CH$_2$Si), 4.16-4.22 (m, 2 H, CHOTBS, C(O)OCH$_2$CH$_2$Si), 3.96 (d, 1 H, J=10.3 Hz, CH$_2$I), 3.83-3.93 (m, 2 H, CH$_2$Cl), 3.65 (d, 1 H, J=10.7 Hz, CH$_2$I), 2.83 (d, 1 H, J=10.7 Hz, CHCH$_2$CH$_2$Cl), 2.65-2.71 (m, 1 H, CH$_2$CH$_2$Cl), 2.14-2.22 (m, 1 H, CH$_2$CH$_2$Cl), 0.94-1.84 (m, 13 H, cyclohexyl, CH$_2$CH$_2$Si), 0.91 (s, 9 H, (CH$_3$)$_3$CSi), 0.19 (s, 6 H, (CH$_3$)$_2$Si), 0.05 (s, 9 H, (CH$_3$)$_3$SiCH$_2$CH$_2$) $^{13}$C NMR (100 MHz, CDCl$_3$)δ: 178.0, 171.5, 79.5, 78.0, 77.5, 65.0, 48.2, 46.1, 43.9, 30.3, 29.7, 29.2, 27.7, 27.5, 26.7, 26.6, 18.8, 17.5, 7.5, −1.4, −2.3, −3.5 HRMS (ESI$^+$): m/z calcd for (C$_{26}$H$_{50}$ClINO$_5$Si$_2$)$^+$ 674.1961, found: 674.1967. FTIR (cm$^{-1}$): 3313, 2952, 2930, 2856, 1717, 1688

Example 8 dried over sodium sulfate and the solids were filtered. The filtrate was concentrated. Purification of the residue by flash column chromatography (20% ethyl acetate-hexanes) gave 2-[(tert-butyl-dimethyl-silanyloxy)-cyclohexyl-methyl]-4-(2-chloro-ethyl)-3-hydroxy-3-methyl-5-oxo-pyrrolidine-2-carboxylic acid 2-trimethyl-silanyl-ethyl ester (48 mg, 74%).

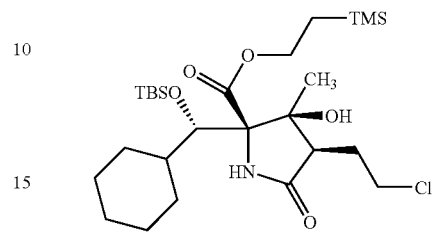

$^1$H NMR (500 MHz, CDCl$_3$)δ: 7.93 (br. s, 1 H, NH), 5.76 (br. s, 1 H, OH), 4.29-4.36 (m, 1 H, C(O)OCH$_2$CH$_2$Si), 4.20 (d, 1 H, J=2.4 Hz, CHOTBS), 4.12-4.19 (m, 1 H, C(O)OCH$_2$CH$_2$Si), 3.81-3.84 (m, 2 H, CH$_2$Cl), 2.80 (dd, 1 H, J=9.3 Hz, J=3.9 Hz, CHCH$_2$CH$_2$Cl), 2.15-2.20 (m, 1 H, CH$_2$CH$_2$Cl), 0.87-1.90 (m, 14 H, CH$_2$CH$_2$Cl, cyclohexyl, CH$_2$CH$_2$Si), 1.50 (s, 3 H, C(OH)CH$_3$), 0.90 (s, 9 H, (CH$_3$)$_3$CSi), 0.17 (s, 6 H, (CH$_3$)$_2$Si), 0.05 (s, 9 H, (CH$_3$)$_3$SiCH$_2$CH$_2$) $^{13}$C NMR (100 MHz, CDCl$_3$)δ: 178.3, 171.9, 81.3, 78.1, 77.4, 64.1, 47.7, 46.4, 44.0, 30.5, 29.3, 27.9, 27.5, 26.8, 26.6, 26.3, 19.8, 18.9, 17.5, −1.4, −2.6, −3.4 HRMS (ESI$^+$): m/z calcd for (C$_{26}$H$_{51}$ClNO$_5$Si$_2$)$^+$ 548.2994, found: 548.2997. FTIR (cm$^{-1}$): 3321, 2930, 2855, 1719, 1685

Example 9

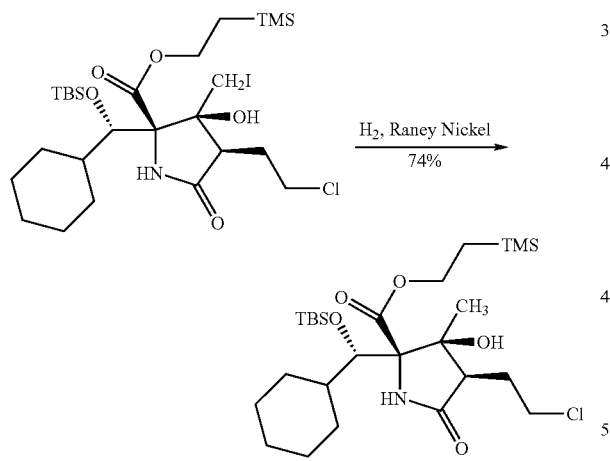

2-[(tert-Butyl-dimethyl-silanyloxy)-cyclohexyl-methyl]-4-(2-chloro-ethyl)-3-hydroxy-3-methyl-5-oxo-pyrrolidine-2-carboxylic acid 2-trimethylsilanyl-ethyl ester Triethylamine (17 μl, 12 mg, 0.119 mmol, 1.0 equiv) was added to a solution of 2-[(tert-butyl-dimethyl-silanyloxy)-cyclohexyl-methyl]-4-(2-chloro-ethyl)-3-hydroxy-3-iodomethyl-5-oxo-pyrrolidine-2-carboxylic acid 2-trimethylsilanyl-ethyl ester (80 mg, 0.119 mmol, 1.0 equiv) in ethyl acetate (5.5 ml) at 23° C., followed by the addition of Raney Nickel solution. Hydrogen balloon was inserted and the resultant heterogeneous solution was vigorously stirred for 2 h. The reaction mixture was filtered through Celite. The filtrate was

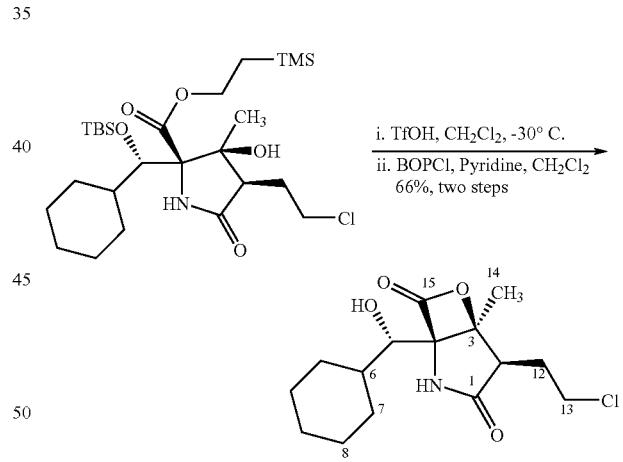

7,8-Dihydrosalinosporamide

Trifluoromethanesulfonic acid (5 μl, 8.2 mg, 0.055 mmol, 5.0 equiv) was added to a solution of 2-[(tert-butyl-dimethylsilanyloxy)-cyclohexyl-methyl]-4-(2-chloro-ethyl)-3-hydroxy-3-methyl-5-oxo-pyrrolidine-2-carboxylic acid 2-trimethylsilanyl-ethyl ester (6 mg, 0.011 mmol, 1.0 equiv) in dichloromethane (1 ml, directly taken from solvent bottles, without drying treatment) at −30° C. The reaction mixture was stirred at that temperature for 10 min. Pyridine (30 μl) was added and the resultant solution was concentrated. The residue obtained was dissolved in dichloromethane (0.2 ml), followed by the addition of pyridine (50 μl) at 23° C. Bis(2- oxo-3-oxazolidinyl)phosphinic chloride (BOPCl, 4.2 mg, 0.0165 mmol, 1.5 equiv) was added and the reaction solution was stirred for 1 h. The solution was concentrated. Purification of the residue by flash column chromatography (40% ethyl acetate-hexanes) afforded 7,8-dihydrosalinosporamide (2.3 mg, 66%) as a white solid.

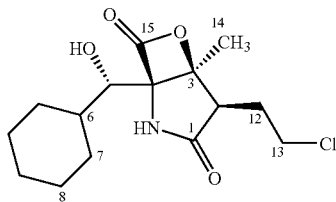

$^1$H NMR (500 MHz, (CD$_3$)S(O)CD$_3$)δ: 9.05 (s, 1 H, NH), 5.27 (d, 1 H, J=7.7 Hz, OH), 3.84-3.92 (m, 2 H, CHOH, CH$_2$Cl), 3.66 (t, 1 H, J=7.9 Hz, CH$_2$Cl), 2.63 (t, 1 H, J=7.2 Hz, CHCH$_2$CH$_2$Cl), 1.94-2.02 (m, 2 H, CH$_2$CH$_2$Cl), 1.55-1.85 (m, 5 H, cyclohexyl), 1.72 (s, 3 H, CH$_3$), 1.45-1.49 (m, 1 H, cyclohexyl), 1.05-1.22 (m, 3 H, cyclohexyl), 0.90-0.95 (m, 2 H, cyclohexyl) $^{13}$C NMR (100 MHz, (CD$_3$)S(O)CD$_3$)δ: 175.9, 169.6, 86.4, 79.6, 70.6, 70.4, 45.9, 45.8, 43.6, 29.8, 29.4, 28.6, 26.3, 20.3, 20.0 HRMS (ESI$^+$): m/z calcd for (C$_{15}$H$_{23}$ClNO$_4$)$^+$ 316.1315, found: 316.1310. FTIR (cm$^{-1}$): 3371, 3322, 2922, 1823, 1701

Example 10

Alkylation Reactions with Different Electrophiles

4-Allyl-2-[(tert-butyl-dimethyl-silanyloxy)-cyclohexyl-methyl]-3-methylene-5-oxo-pyrrolidine-2-carboxylic acid methyl ester Lithium diisopropylamide solution (0.695 M solution in tetrahydrofuran, 5.66 ml, 3.93 mmol, 1.0 equiv) was added dropwise via syringe to a stirred solution of 2-[(tert-butyl-dimethyl-silanyloxy)-cyclohexyl-methyl]-3-methyl-5-oxo-2,5-dihydro-1H-pyrrole-2-carboxylic acid methyl ester (1.5 g, 3.93 mmol, 1.0 equiv) in tetrahydrofuran (45 ml) at −78° C. The reaction mixture was stirred at −78° C. for 30 min. Chlorotrimethylsilane (0.5 ml, 427 mg, 3.93 mmol, 1.0 equiv) was added and the resultant solution was stirred at −78° C. for 3 h. Another equiv of lithium diisopropylamide solution (0.695 M solution in tetrahydrofuran, 5.66 ml, 3.93 mmol, 1.0 equiv) was added dropwise at −78° C. The reaction mixture was stirred −78° C. for 30 min. Allyl bromide (0.68 ml, 0.951 g, 7.86 mmol, 2.0 equiv) was added dropwise via syringe at −78° C. The reaction mixture was stirred at −78° C. for 2 h. A buffer solution (pH=7, 100 ml) was added at −78° C. The mixture was extracted with ethyl acetate (50 ml×3). The combined organic layers were dried over sodium sulfate and the solids were filtered. The filtrate was concentrated. The residue was purified by flash column chromatography (10% ethyl acetate-hexanes initially, grading to 20% ethyl acetate-hexanes) to furnish 4-allyl-2-[(tert-butyl-dimethyl-silanyloxy)-cyclohexyl-methyl]-3-methylene-5-oxo-pyrrolidine-2-carboxylic acid methyl ester (0.757 g, 46%) as a white solid.

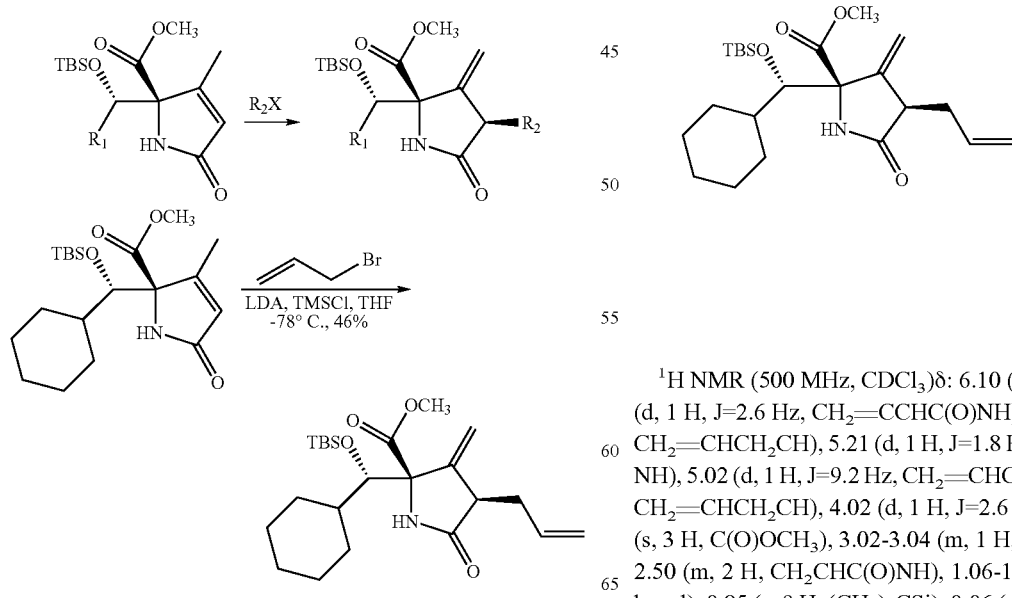

$^1$H NMR (500 MHz, CDCl$_3$)δ: 6.10 (br. s, 1 H, NH), 5.63 (d, 1 H, J=2.6 Hz, CH$_2$=CCHC(O)NH), 5.58-5.70 (m, 1 H, CH$_2$=CHCH$_2$CH), 5.21 (d, 1 H, J=1.8 Hz, CH$_2$=CCHC(O)NH), 5.02 (d, 1 H, J=9.2 Hz, CH$_2$=CHCH$_2$CH), 4.97 (s, 1 H, CH$_2$=CHCH$_2$CH), 4.02 (d, 1 H, J=2.6 Hz, CHOTBS), 3.71 (s, 3 H, C(O)OCH$_3$), 3.02-3.04 (m, 1 H, CHC(O)NH), 2.46-2.50 (m, 2 H, CH$_2$CHC(O)NH), 1.06-1.70 (m, 11 H, cyclohexyl), 0.85 (s, 9 H, (CH$_3$)$_3$CSi), 0.06 (s, 3 H, CH$_3$Si), −0.03 (s, 3 H, CH$_3$Si)

Enantioselective Synthesis of 7,8-dihydrosalinosporamide
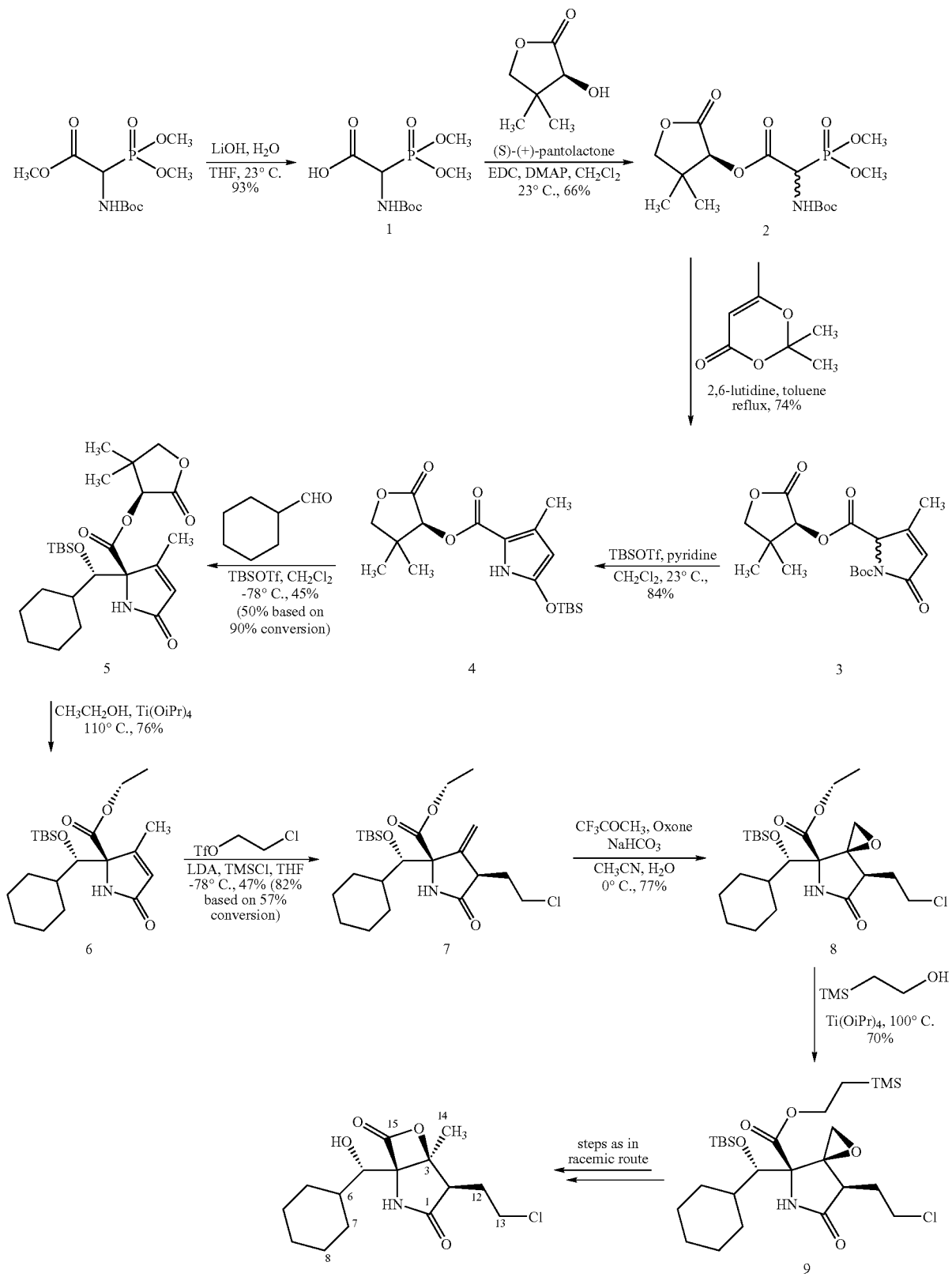

Compound 2:

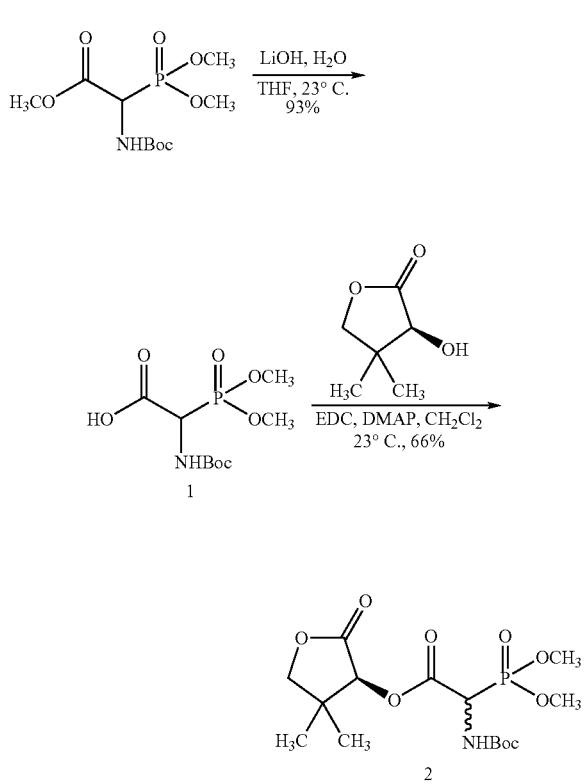

Aqueous lithium hydroxide solution (1.0 M, 37 ml) was added dropwise to a stirring solution of tert-butoxycarbonylamino-(dimethoxy-phosphoryl)-acetic acid methyl ester (10.0 g, 33.5 mmol, 1.0 equiv) in tetrahydrofuran (100 ml) at 0° C. When the addition is complete, the resultant solution was warmed to 23° C. and stirred at this temperature for 1 h. Aqueous hydrochloric acid solution (0.5 M) was added dropwise to change the pH to 2. The resultant solution was extracted with three 50 ml portions of ethyl acetate. The combined organic layers were washed with two 25 ml portions of saturated sodium chloride solution, dried over sodium sulfate. The solids were filtered and the filtrate was concentrated. The acid 1 (8.8 g, 93%) was used directly in the next step. 1-Ethyl-3-(3'-dimethylaminopropyl)carbodiimide hydrochloride (225 mg, 1.18 mmol, 0.8 equiv) and 4-dimethylaminopyridine (36 mg, 0.29 mmol, 0.2 equiv) was added to a solution of acid 1 (333 mg, 1.18 mmol, 0.8 equiv) and (S)-(+)-pantolactone (192 mg, 1.47 mmol, 1.0 equiv) in dichloromethane at 23° C. The mixture was stirred at 23° C. for 8 h. 1-Ethyl-3-(3'-dimethylaminopropyl)carbodiimide hydrochloride (225 mg, 1.18 mmol, 0.8 equiv) and acid 1 (333 mg, 1.18 mmol, 0.8 equiv) was added at 23° C. and the reaction mixture was stirred at this temperature for 20 h. Saturated sodium chloride solution (10 ml) was added and the resultant mixture was extracted with four 10 ml portions of dichloromethane. The combined organic layers were dried over sodium sulfate and the solids were filtered. The filtrate was concentrated. Purification of the residue by flash column chromatography (60% ethyl acetate-hexanes initially, grading to 95% ethyl acetate-hexanes) provided pantolactone ester 2 as a colorless oil (385 mg, 66%).

$^1$H NMR (500 MHz, CDCl$_3$)δ: Two diastereoisomers (~1.04:1), * donates minor diastereoisomer. 5.47 (s, 1 H*, OCHC(O)O), 5.42-5.46 (m, 1 H and 1 H*, NH), 5.42 (s, 1 H, OCHC(O)O), 5.06 (dd, 1 H, J=22.6 Hz, 8.5 Hz, CHP(O) (OCH$_3$)$_2$), 4.93 (dd, 1 H*, J=23.1 Hz, 9.1 Hz, CHP(O) (OCH$_3$)$_2$), 4.06-4.12 (m, 2 H and 2 H*, C(O)OCH$_2$), 3.88-3.91 (m, 6 H and 6 H*, P(O)(OCH$_3$)$_2$), 1.49 (s, 9 H and 9 H*, C(O)OC(CH$_3$)$_3$), 1.27 (s, 3 H and 3 H*, CH$_3$CCH$_2$O), 1.22 (s, 3 H*, CH$_3$CCH$_2$O), 1.21 (s, 3 H, CH$_3$CCH$_2$O) $^{13}$C NMR (100 MHz, CDCl$_3$)δ: Two diastereoisomers. 171.5, 171.3, 166.7, 166.5, 155.2, 154.8, 81.3, 81.2, 76.8, 76.3, 54.5, 54.4, 54.2, 52.9, 52.7, 51.4, 51.3, 40.8, 40.7, 28.4, 28.3, 23.1, 22.8, 19.9, 19.8 HRMS (ESI$^+$): m/z calcd for (C$_{15}$H$_{27}$NO$_9$P)$^+$ 396.1423, found: 396.1422. FTIR (cm$^{-1}$): 3268, 2969, 1793, 1759, 1711

Compound 3:

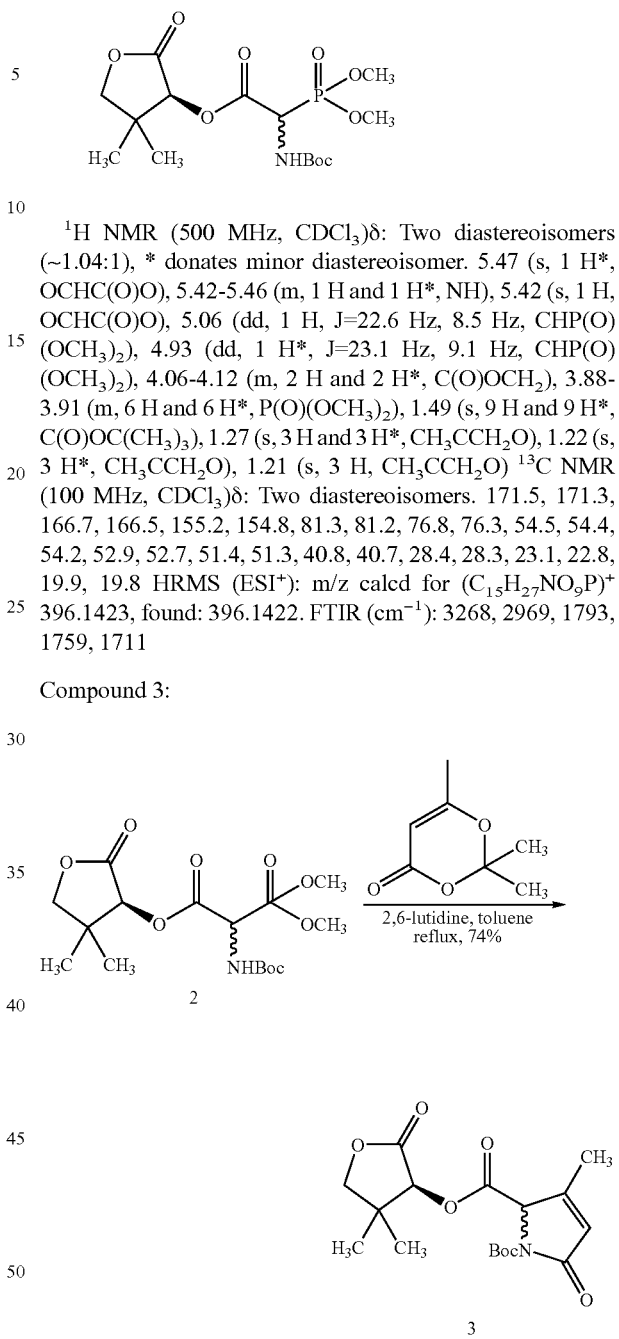

A solution of pantolactone ester 2 (7.66 g, 19.4 mmol, 1.0 equiv), 2,2,6-trimethyl-[1,3]dioxin-4-one (12.66 ml, 13.78 g, 97.0 mmol, 5.0 equiv), and 2,6-lutidine (3.39 ml, 3.12 g, 29.1 mmol, 1.5 equiv) in toluene (125 ml) was heated at reflux for 15 h. The reaction mixture was allowed to cool to 23° C. and was concentrated. The residue was purified by flash column chromatography (20% ethyl acetate-hexanes initially, grading to 30% ethyl acetate-hexanes, then to 40% ethyl acetate-hexanes) to give 3 (5.11 g, 74%) as a yellow oil.

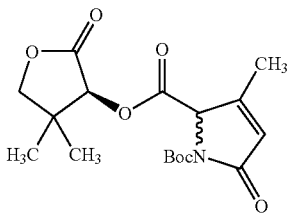

¹H NMR (500 MHz, CDCl₃)δ: Two diastereoisomers (~1.4:1), * donates minor diastereoisomer. 5.93-5.94 (m, 1 H*, NCHC(O)O), 5.91-5.93 (m, 1 H, NCHC(O)O), 5.41 (s, 1 H, OCHC(O)O), 5.35 (s, 1 H*, OCHC(O)O), 5.04 (d, 1 H, J=1.0 Hz, CHC(O)N), 5.02 (d, 1 H*, J=1.0 Hz, CHC(O)N), 4.02-4.08 (m, 2 H and 2 H*, C(O)OCH₂), 2.18 (s, 3 H, CH₃CCHC(O)N), 2.14 (s, 3 H*, CH₃CCHC(O)N), 1.51 (s, 9 H, (CH₃)₃COC(O)N), 1.50 (s, 9 H*, (CH₃)₃COC(O)N), 1.22 (s, 3 H, CH₃CCH₂O), 1.18 (s, 3 H*, CH₃CCH₂O), 1.14 (s, 3H, CH₃CCH₂O), 1.06 (s, 3 H*, CH₃CCH₂O) ¹³C NMR (100 MHz, CDCl₃)δ: Two diastereoisomers. 171.5, 171.2, 168.1, 168.0, 166.5, 166.1, 155.4, 155.2, 149.1, 149.0, 124.7, 124.6, 84.1, 84.0, 76.6, 76.5, 76.4, 76.3, 67.3, 66.4, 40.6, 40.1, 28.3, 28.2, 23.0, 22.9, 20.1, 20.0, 15.0, 14.8 HRMS (ESI⁺): m/z calcd for (C₁₇H₂₄NO₇)⁺ 354.1553, found: 354.1559. FTIR (cm⁻¹): 2977, 2935, 1786, 1748, 1710, 1646

Compound 4:

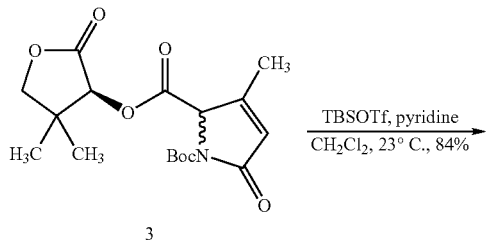

tert-Butyldimethylsilyltrifluoromethanesulfonate (6.63 ml, 7.63 g, 28.86 mmol, 2.0 equiv) was added to a stirring solution of 3 (5.1 g, 14.4 mmol, 1.0 equiv) and pyridine (4.67 ml, 4.57 g, 57.7 mmol, 4.0 equiv) in dichloromethane (100 ml) at 23° C. The mixture was stirred at 23° C. for 1 h, and tert-butyldimethylsilyltrifluoromethanesulfonate (6.63 ml, 7.63 g, 28.86 mmol, 2.0 equiv) was added. The resultant solution was stirred at 23° C. for 19 h. The reaction mixture was cooled to −78° C. and quenched with saturated sodium bicarbonate solution (100 ml). The organic layer was separated. The aqueous layer was extracted with three 50 ml portions of dichloromethane. The combined organic layers were dried over sodium sulfate. The solids filtered and the filtrate was concentrated. The residue was purified by flash column chromatography (10% ethyl acetate-hexanes initially, grading to 15% ethyl acetate-hexanes) to afford 4 (4.5 g, 84%) as a colorless oil.

¹H NMR (500 MHz, CDCl₃)δ: 8.38 (br. s, 1 H, NH), 5.55 (s, 1 H, OCHC(O)O), 5.24 (d, 1 H, J=2.9 Hz, CHC(NH) OTBS), 4.07 (d, 1 H, J=9.3 Hz, C(O)OCH₂), 4.04 (d, 1 H, J=8.8 Hz, C(O)OCH₂), 2.29 (s, 3 H, CH₃CCHCOTBS), 1.23 (s, 3 H, CH₃CCH₂O), 1.16 (s, 3 H, CH₃CCH₂O), 0.95 (s, 9 H, (CH₃)₃CSi), 0.24 (s, 6H, (CH₃)₂Si) ¹³C NMR (100 MHz, CDCl₃)δ: 173.5, 159.5, 146.6, 132.0, 108.6, 96.1, 76.4, 74.4, 40.6, 25.7, 23.3, 20.5, 18.3, 13.8, −4.6 HRMS (ESI⁺): m/z calcd for (C₁₈H₃₀NO₅Si)⁺ 368.1893, found: 368.1885. FTIR (cm⁻¹): 3298, 2959, 2931, 2860, 1788, 1678, 1581, 1510

Compound 5:

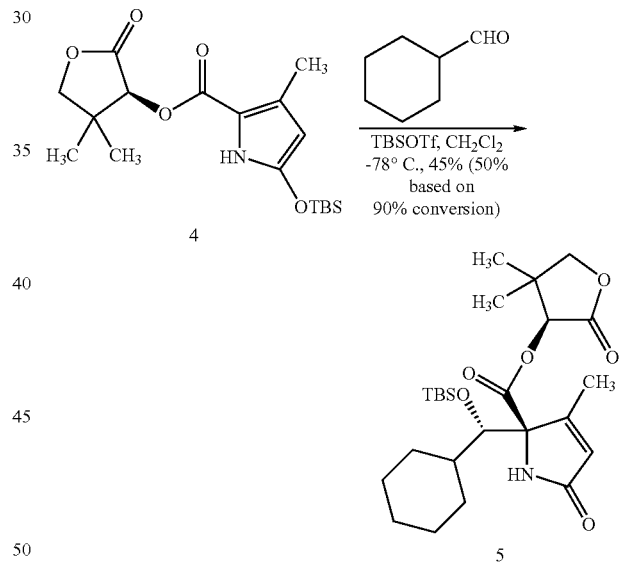

tert-Butyldimethylsilyltrifluoromethanesulfonate (119 μl, 136.7 mg, 0.52 mmol, 2.0 equiv) was added dropwise to a stirring solution of 4 (95 mg, 0.26 mmol, 1.0 equiv) and cyclohexanecarbaldehyde (47 μl, 44 mg, 0.39 mmol, 1.5 equiv) in dichloromethane (2.6 ml) at −78° C. The resultant solution was stirred at −78° C. for 6 h, and quenched with triethylamine (109 μl, 79 mg, 0.78 mmol, 3.0 equiv) at −78° C. Saturated sodium bicarbonate solution (40 ml) was added at −78° C. The organic layer was separated and the aqueous layer was extracted with three 40 ml portions of dichloromethane. The combined organic layers were dried over sodium sulfate. The solids were filtered and the filtrate was concentrated. The residue obtained was purified by flash column chromatography (20% ethyl acetate-hexanes initially, grading to 35% ethyl acetate-hexanes) to give a mixture of the desired diastereoisomer 5 and a minor diastereoisomer (Note: this mixture can be used directly in the next step. The minor diastereoisomer can be readily removed by flash column chromatography in the next step). This mixture was purified by flash column chromatography (10% ethyl acetate-dichloromethane initially, grading to 15% ethyl acetate-dichloromethane) to give 5 (56 mg, 45%) as a colorless oil (Note: 10 mg starting 4 was recovered (10%), and the yield is 50% based on recovered starting material. Four diastereoisomers was isolated (1:0.31:0.28:0.26, total yield: 84%), and the major diastereoisomer is the desired one).

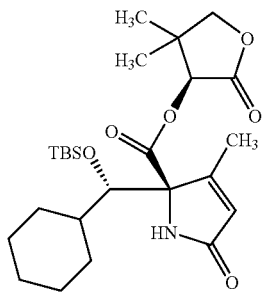

$^1$H NMR (500 MHz, CDCl$_3$)δ: 6.57 (br. s, 1 H, NH), 5.87 (d, 1 H, J=10 Hz, CHC(O)NH), 5.32 (s, 1 H, OCHC(O)O), 4.28 (s, 1 H, CHOTBS), 3.99-4.04 (m, 2 H, C(O)OCH$_2$), 2.20 (s, 3 H, CH$_3$CCHC(O)NH), 1.07-1.75 (m, 11 H, cyclohexyl), 1.19 (s, 3 H, CH$_3$CCH$_2$O), 1.04 (s, 3 H, CH$_3$CCH$_2$O), 0.86 (s, 9 H, (CH$_3$)$_3$CSi), 0.13 (s, 3 H, CH$_3$Si), 0.02 (s, 3 H, CH$_3$Si) $^{13}$C NMR (100 MHz, CDCl$_3$)δ: 173.6, 171.2, 169.2, 159.8, 125.5, 77.7, 76.4, 76.3, 75.9, 41.0, 40.6, 32.2, 28.0, 27.0, 26.5, 26.3, 26.2, 23.2, 20.0, 18.8, 16.1, −3.4, −4.1 HRMS (ESI$^+$): m/z calcd for (C$_{25}$H$_{45}$N$_2$O$_6$Si)$^+$ 497.3047, found: 497.3047. FTIR (cm$^{-1}$): 3190, 2928, 2855, 1793, 1744, 1701

Compound 6:

heated at 110° C. for 6 h in microwave. The reaction mixture was allowed to cool to 23° C. and ethyl acetate (60 ml) and water (30 ml) was added. The resultant solution was stirred for 10 min and filtered through Celite. The organic layer was separated and the aqueous layer was extracted with ethyl acetate (60 ml×2). The combined organic layers were dried over sodium sulfate and the solids were filtered. The filtrate was concentrated. The residue was purified by flash column chromatography (7% ethyl acetate-dichloromethane initially, grading to 10% ethyl acetate-dichloromethane) to afford 6 (95 mg, 76%) as a colorless oil.

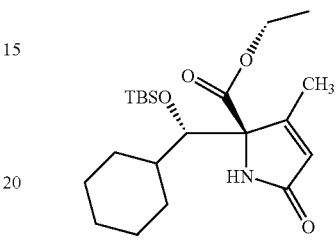

$^1$H NMR (500 MHz, CDCl$_3$)δ: 6.34 (br. s, 1 H, NH), 5.81 (d, 1 H, J=1.5 Hz, CHC(O)NH), 4.15-4.20 (m, 3 H, CHOTBS, C(O)OCH$_2$CH$_3$), 2.16 (s, 3 H, CH$_3$CCHC(O)NH), 1.03-1.73 (m, 11 H, cyclohexyl), 1.26 (t, 3 H, J=6.8 Hz, C(O) OCH$_2$CH$_3$), 0.85 (s, 9 H, (CH$_3$)$_3$CSi), 0.10 (s, 3H, CH$_3$Si), −0.01 (s, 3H, CH$_3$Si) $^{13}$C NMR (100 MHz, CDCl$_3$)δ: 173.4, 169.4, 160.1, 125.2, 78.4, 75.7, 62.3, 40.9, 32.2, 28.0, 27.0, 26.6, 26.3, 26.2, 18.7, 16.4, 14.1, −3.3, −4.4 HRMS (ESI$^+$): m/z calcd for (C$_{21}$H$_{38}$NO$_4$Si)$^+$ 396.2570, found: 396.2553. FTIR (cm$^{-1}$): 3201, 2928, 2855, 1740, 1701

Compound 7:

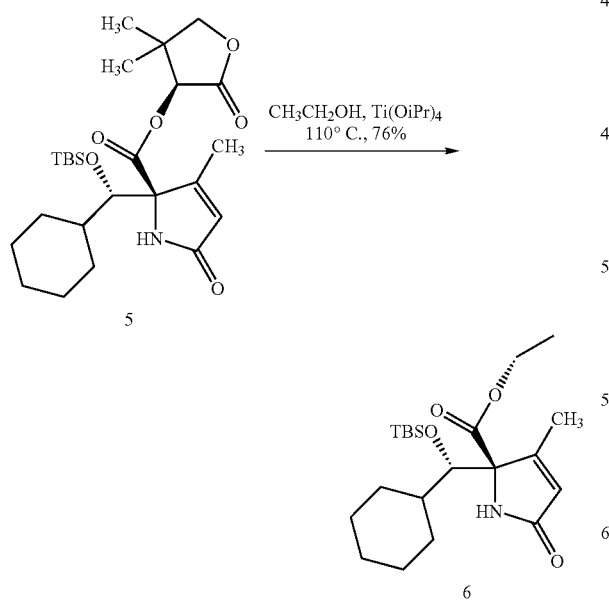

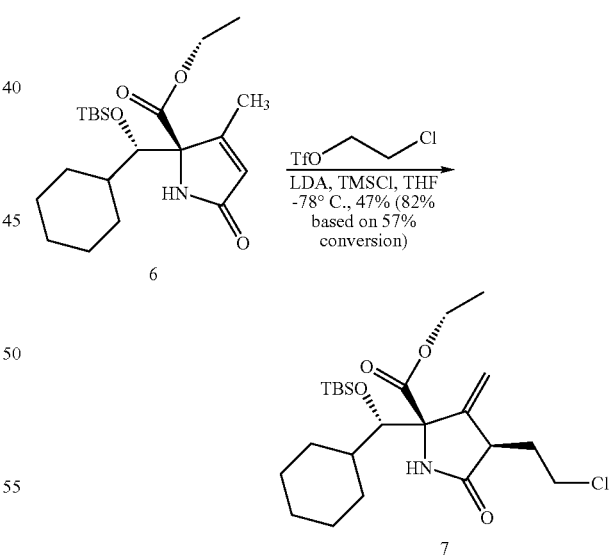

Titanium (IV) isopropoxide (1.0 ml) was added to a stirred solution of pantolactone ester (152 mg, 0.317 mmol, 1.0 equiv) in ethanol (4.5 ml), and the resultant solution was Lithium diisopropylamide solution (0.80 M solution in tetrahydrofuran, 0.593 ml, 0.475 mmol, 1.0 equiv) was added dropwise via syringe to a stirred solution of 6 (188 mg, 0.475 mmol, 1.0 equiv) in tetrahydrofuran (6.0 ml) at −78° C. The reaction mixture was stirred at −78° C. for 30 min. Chlorotrimethylsilane (60 µl, 51.6 mg, 0.475 mmol, 1.0 equiv) was added and the resultant solution was stirred at −78° C. for 2 h. Another equiv of lithium diisopropylamide solution (0.80 M solution in tetrahydrofuran, 0.593 ml, 0.475 mmol, 1.0 equiv) was added dropwise at −78° C. The reaction mixture was stirred −78° C. for 30 min. A stock solution of trifluoromethanesulfonic acid 2-chloro-ethyl ester in toluene (3.04 M, 0.625 ml, 1.9 mmol, 4.0 equiv) was added dropwise via syringe at −78° C. The reaction mixture was stirred at −78° C. for 90 min. A buffer solution (pH=7, 30 ml) was added at −78° C. The organic layer was separated, washed with brine solution (10 ml), dried over sodium sulfate and the solids were filtered. The filtrate was concentrated. The residue was purified by flash column chromatography (10% ethyl acetate-hexanes initially, grading to 20% ethyl acetate-hexanes) to furnish compound 7 (103 mg, 47%) along with recovered starting material (80 mg, 43%).

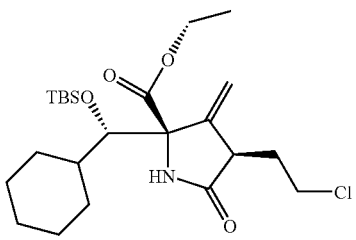

$^1$H NMR (500 MHz, CDCl$_3$)δ: 6.16 (br. s, 1 H, NH), 5.68 (d, 1 H, J=2.4 Hz, CH$_2$CCHC(O)NH), 5.22 (d, 1 H, J=1.0 Hz, CH$_2$CCHC(O)NH), 4.17-4.27 (m, 2 H, C(O)OCH$_2$CH$_3$), 4.04 (d, 1 H, J=2.0 Hz, CHOTBS), 3.73-3.78 (m, 1 H, CH$_2$Cl), 3.58-3.63 (m, 1H, CH$_2$Cl), 3.14-3.17 (m, 1 H, CHC(O)NH), 2.08-2.16 (m, 2 H, CH$_2$CH$_2$Cl), 1.06-1.75 (m, 11 H, cyclohexyl), 1.28 (t, 3 H, J=7.3 Hz, C(O)OCH$_2$CH$_3$), 0.87 (s, 9 H, (CH$_3$)$_3$CSi), 0.09 (s, 3H, CH$_3$Si), −0.01 (s, 3H, CH$_3$Si) $^{13}$C NMR (100 MHz, CDCl$_3$)δ: 176.6, 170.9, 146.3, 112.0, 81.1, 73.7, 62.2, 43.4, 42.9, 41.8, 34.6, 31.8, 29.0, 27.1, 26.8, 26.4, 26.3, 18.7, 14.2, −3.6, −3.7 HRMS (ESI$^+$): m/z calcd for (C$_{23}$H$_{41}$ClNO$_4$Si)$^+$ 458.2493, found: 458.2484. FTIR (cm$^{-1}$): 3197, 2929, 2856, 1706, 1659

Compound 8:

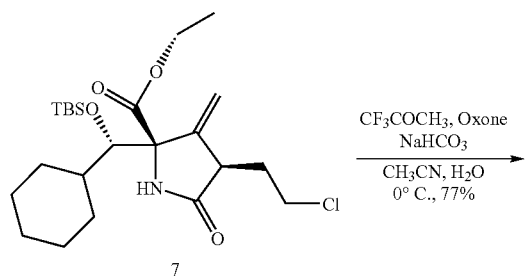

An aqueous ethylenediaminetetraacetic acid disodium solution (2.0 ml, 4×10$^{-4}$ M) was added to a stirred solution of 7 (96 mg, 0.21 mmol, 1.0 equiv) in acetonitrile (5.0 ml) and the reaction mixture was cooled to 0° C. Trifluoroacetone (1.0 ml) was added via a precooled syringe. A mixture of sodium bicarbonate (0.273 g, 3.25 mmol, 15.5 equiv) and Oxone (0.644 g, 1.05 mmol, 5.0 equiv) was added. The reaction mixture was stirred for 2 h at 0° C. Trifluoroacetone (0.4 ml) was added via a precooled syringe, followed by the addition of a mixture of sodium bicarbonate (0.273 g, 3.25 mmol, 15.5 equiv) and Oxone (0.644 g, 1.05 mmol, 5.0 equiv). The reaction mixture was stirred for 1 h at 0° C. Water (20 ml) was added and the resultant mixture was extracted with dichloromethane (50 ml). The organic layer was separated and the aqueous layer was extracted with dichloromethane (30 ml×2). The combined organic layers were dried over sodium sulfate and the solids were filtered. The filtrate was concentrated. Purification of the residue by flash column chromatography (15% ethyl acetate-hexanes initially, grading to 20% ethyl acetate-hexanes) provided compound 8 (77 mg, 77%).

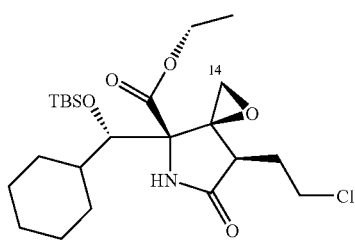

$^1$H NMR (500 MHz, CDCl$_3$)δ: 6.22 (s, 1 H, NH), 4.21-4.27 (m, 1 H, C(O)OCH$_2$CH$_3$), 4.12-4.18 (m, 1 H, C(O)OCH$_2$CH$_3$), 4.07 (d, 1 H, J=3.4 Hz, CHOTBS), 3.86-3.91 (m, 1 H, CH$_2$Cl), 3.62-3.66 (m, 1 H, CH$_2$Cl), 3.21 (d, 1H, J=3.9 Hz, C (14)-H), 3.18-3.21 (m, 1 H, CHC(O)NH), 2.86 (d, 1 H, J=3.4 Hz, C (14)-H), 1.96-2.02 (m, 1 H, CH$_2$CH$_2$Cl), 0.96-1.75 (m, 12 H, cyclohexyl, CH$_2$CH$_2$Cl), 1.29 (t, 3 H, J=6.8 Hz, C(O)OCH$_2$CH$_3$), 0.93 (s, 9 H, (CH$_3$)$_3$CSi), 0.16 (s, 3 H, CH$_3$Si), 0.09 (s, 3 H, CH$_3$ Si) $^{13}$C NMR (100 MHz, CDCl$_3$)δ: 176.3, 167.8, 78.6, 72.9, 64.3, 62.1, 46.3, 44.5, 43.1, 39.3, 31.0, 30.0, 28.2, 27.2, 27.1, 26.5, 26.3, 18.5, 14.3, −3.2, −3.4 HRMS (ESI$^+$): m/z calcd for (C$_{23}$H$_{41}$ClNO$_5$Si)$^+$ 474.2442, found: 474.2459. FTIR (cm$^{-1}$): 3192, 3086, 2931, 2856, 1706

Compound 9:

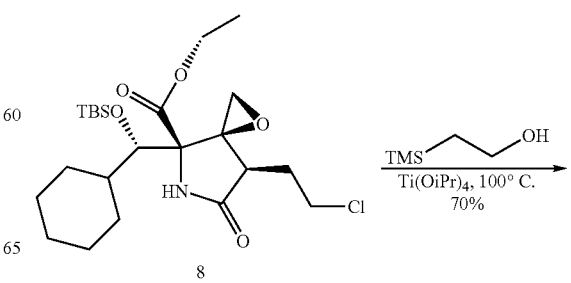

-continued

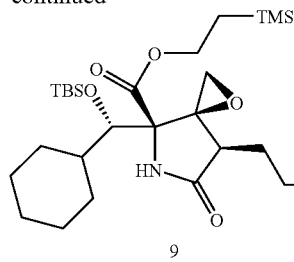
9

Titanium (IV) isopropoxide (0.36 ml, 0.50 g, 1.8 mmol, 11.1 equiv) was added to a stirred solution of 8 (77 mg, 0.162 mmol, 1.0 equiv) in 2-trimethylsilanyl-ethanol (1.8 ml), and the resultant solution was heated at 100° C. for 18 h. The reaction mixture was allowed to cool to 23° C. and ethyl acetate (30 ml) and water (20 ml) was added. The resultant solution was stirred for 10 min and filtered through Celite. The organic layer was separated and the aqueous layer was extracted with ethyl acetate (15 ml×2). The combined organic layers were dried over sodium sulfate and the solids were filtered. The filtrate was concentrated. The residue was purified by flash column chromatography (10% ethyl acetate-hexanes initially, grading to 15% ethyl acetate-hexanes) to afford compound 9 (62 mg, 70%) as a colorless oil.

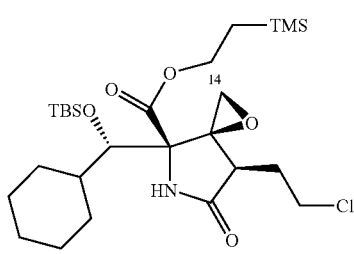
14

$^1$H NMR (500 MHz, CDCl$_3$) δ: 7.10 (s, 1 H, NH), 4.11-4.25 (m, 2 H, C(O)OCH$_2$CH$_2$Si), 4.06 (d, 1 H, J=2.0 Hz, CHOTBS), 3.84-3.88 (m, 1 H, CH$_2$Cl), 3.60-3.64 (m, 1 H, CH$_2$Cl), 3.18 (s, 1 H, C (14)-H), 3.16 (t, 1 H, J=6.6 Hz, CHC(O)NH), 2.82 (s, 1 H, C (14)-H), 1.91-1.98 (m, 1 H, CH$_2$CH$_2$Cl), 1.04-1.70 (m, 12 H, cyclohexyl, CH$_2$CH$_2$Cl), 1.00 (t, 2 H, J=9.3 Hz, CH$_2$CH$_2$Si), 0.90 (s, 9 H, (CH$_3$)$_3$CSi), 0.14 (s, 3 H, CH$_3$Si), 0.06 (s, 3H, CH$_3$Si), 0.02 (s, 9 H, (CH$_3$)$_3$Si) $^{13}$C NMR (100 MHz, CDCl$_3$) δ: 176.5, 168.0, 78.7, 73.1, 64.5, 64.3, 46.3, 44.0, 43.1, 39.3, 31.0, 29.8, 28.3, 27.2, 26.9, 26.5, 26.4, 18.5, 17.5, −1.3, −3.1, −3.4 HRMS (ESI$^+$): m/z calcd for (C$_{26}$H$_{49}$ClNO$_5$Si$_2$)$^+$ 546.2838, found: 546.2831. FTIR (cm$^{-1}$): 3188, 3097, 2929, 2857, 1706

Additional Concepts:

Although in the enantioselective route we used (S)-(−)-pantolactone as the chiral auxiliary, it is possible to use the less expensive (R)-(+)-pantolactone as the chiral auxiliary.

In the first reaction shown below, (R)-(−)-pantolactone is coupled to the acid to form the (S)-(+)-pantolactone ester under the Mitsunobu condition.

In the second reaction, the triflate ester of (R)-(−)-pantolactone is coupled to the acid to form the (S)-(+)-pantolactone ester via a S$_N$2 substitution.

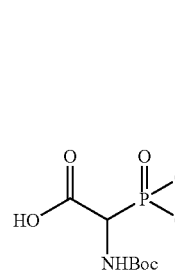

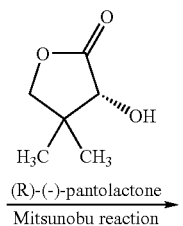

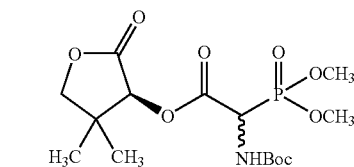

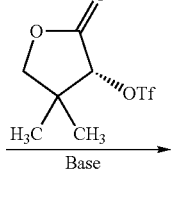

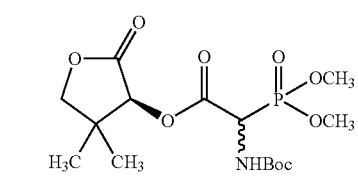

The present invention has been described in detail, including the preferred embodiments thereof. However, it will be appreciated that those skilled in the art, upon consideration of the present disclosure, may make modifications and/or improvements on this invention and still be within the scope of this invention as set forth in the following claims.

What is claimed is:

1. Nucleophilic substituted analogs of Salinosporamide A, having the Formula Ia:

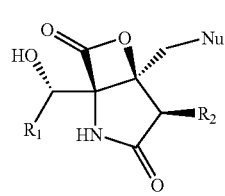

Ia wherein:
R$_1$ is selected from the group consisting of methyl, ethyl, propyl, iso-propyl, n-butyl, iso-butyl, and tert-butyl, each optionally substituted by halogen
R$_2$ is selected from the group consisting of substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted, saturated or unsaturated, C$_3$-C$_8$ cycloalkyl, benzyl and substituted benzyl; wherein the substituent groups are independently selected from the group consisting of C$_1$-C$_4$ alkoxy, amido, halogen and aryl; and Nu is a Nucleophile selected from the group consisting of:
carb-sulfides having the formula RS— wherein R can be substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted, saturated or unsaturated, $C_3$-$C_8$ cycloalkyl, benzyl and substituted benzyl; wherein the substituent groups are independently selected from the group consisting of $C_1$-$C_4$ alkoxy, amido, halogen and aryl;
cyanide having the formula CN—;
azide having the formula $N_3$—;
carboxylates having the formula $RCO_2$—, wherein R can be substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted, saturated or unsaturated, $C_3$-$C_8$ cycloalkyl, benzyl and substituted benzyl; wherein the substituent groups are independently selected from the group consisting of $C_1$-$C_4$ alkoxy, amido, halogen and aryl;
substituted $C_1$-$C_8$ alkyl; substituted or unsubstituted $C_2$-$C_8$ alkenyl; substituted or unsubstituted $C_2$-$C_8$ alkynyl; substituted or unsubstituted, saturated or unsaturated, $C_3$-$C_8$ cycloalkyl; benzyl and substituted benzyl; wherein the substituent groups for each are independently selected from the group consisting of $C_1$-$C_4$ alkoxy, amido, halogen and aryl; and
$NH_3$, hydrazine, water, polyamines, polyols, amino alcohols, amino thiols, dithiols, thioacetamides, acetamidine, carbon monoxide, carbonate having the formula $CO_3$, acetate having the formula $CH_3CO$; and dithiocarbamates.

2. Analogs of Salinosporamide A, having the Formula IIa:

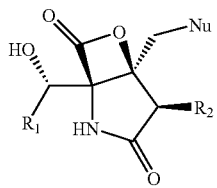

IIa wherein:
$R_1$ is selected from the group consisting of methyl, ethyl, propyl, iso-propyl, n-butyl, iso-butyl, and tert-butyl, each optionally substituted by halogen;
$R_2$ is selected from the group consisting of substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted, saturated or unsaturated, $C_3$-$C_8$ cycloalkyl, benzyl and substituted benzyl; wherein the substituent groups are independently selected from the group consisting of $C_1$$C_{-4}$ alkoxy, amido, halogen and aryl; and
Nu is $R_3$, which is selected from the group consisting of substituted $C_1$-$C_8$ alkyl, substituted or unsubstituted $C_2$-$C_8$ alkenyl, substituted or unsubstituted $C_2$-$C_8$ alkynyl, substituted or unsubstituted, saturated or unsaturated, $C_3$-$C_8$ cycloalkyl, benzyl and substituted benzyl; wherein the substituent groups are independently selected from the group consisting of $C_1$-$C_4$ alkoxy, amido, halogen and aryl.

3. A pharmaceutical composition comprising a compound of claim 1 and a pharmaceutically acceptable carrier or diluent.

4. A method of inhibiting proteasome function in a mammalian cell comprising administering to a mammal an effective proteasome inhibiting amount of the composition of claim 3.

5. The method of claim 4, where the mammalian cell is a human cell.

6. A method of inhibiting inflammation in mammals comprising administering to a mammal an effective anti-inflammatory amount of the composition of claim 3.

7. The method of claim 6, where the mammal is a human.

8. A method of treating ischemic or reperfusion injury in mammals comprising administering to a mammal an effective amount of the composition of claim 3.

9. The method of claim 8, where the mammal is a human.

10. A pharmaceutical composition comprising a compound of claim 2 and a pharmaceutically acceptable carrier or diluent.

11. A method of inhibiting proteasome function in a mammalian cell comprising administering to a mammal an effective proteasome inhibiting amount of the composition of claim 10.

12. The method of claim 11, where the mammalian cell is a human cell.

13. A method of inhibiting inflammation in mammals comprising administering to a mammal an effective anti-inflammatory amount of the composition of claim 10.

14. The method of claim 13, where the mammal is a human.

15. A method of treating ischemic or reperfusion injury in mammals comprising administering to a mammal an effective amount of the composition of claim 10.

16. The method of claim 15, where the mammal is a human.

* * * * *

UNITED STATES PATENT AND TRADEMARK OFFICE
CERTIFICATE OF CORRECTION

Page 1 of 1

PATENT NO. : 7,691,896 B2
APPLICATION NO. : 12/028024
DATED : April 6, 2010
INVENTOR(S) : Andrew G. Myers, Binyuan Sun and Stona R. Jackson It is certified that error appears in the above-identified patent and that said Letters Patent is hereby corrected as shown below:

At Column 1, line 19, please replace "R37-CA04148" with --CA047148-- in the grant number from the NIH.

Signed and Sealed this
Eleventh Day of September, 2012

David J. Kappos
*Director of the United States Patent and Trademark Office*